(12) United States Patent
Boustany

(10) Patent No.: US 8,242,086 B2
(45) Date of Patent: Aug. 14, 2012

(54) METHODS AND COMPOSITIONS FOR TREATING DISORDERS CAUSED BY A DEFICIENCY IN A GENE PRODUCT OF A CLN GENE

(75) Inventor: Rose-Mary N. Boustany, Beirut (LB)

(73) Assignees: Duke University, Durham, NC (US); The American University of Beirut, Beirut (LB)

( * ) Notice: Subject to any disclaimer, the term of this patent is extended or adjusted under 35 U.S.C. 154(b) by 158 days.

(21) Appl. No.: 12/617,318

(22) Filed: Nov. 12, 2009

(65) Prior Publication Data

US 2010/0152123 A1 Jun. 17, 2010

Related U.S. Application Data

(60) Provisional application No. 61/113,676, filed on Nov. 12, 2008, provisional application No. 61/116,481, filed on Nov. 20, 2008.

(51) Int. Cl.
*A61K 31/7032* (2006.01)
*A61K 31/7028* (2006.01)
*A61K 48/00* (2006.01)
*C07H 15/10* (2006.01)
*C07H 21/02* (2006.01)
*C07H 21/04* (2006.01)

(52) U.S. Cl. ........ 514/25; 514/44 R; 536/17.9; 536/23.2
(58) Field of Classification Search .................. None
See application file for complete search history.

(56) References Cited

U.S. PATENT DOCUMENTS

| 5,846,947 | A | * | 12/1998 | Behr et al. ............ 514/44 A |
| 6,821,995 | B1 | | 11/2004 | Boustany |
| 7,129,043 | B1 | | 10/2006 | Boustany et al. |
| 8,003,327 | B2 | | 8/2011 | Boustany et al. |

FOREIGN PATENT DOCUMENTS

WO WO2008/154198 * 12/2008

OTHER PUBLICATIONS

Cross, "Cell Cycle Arrest Caused by CLN Gene Deficiency in Saccharomyces cerevisiae Resembles START-I Arrest and is Independent of the Mating-Pheromone Signalling Pathway" *Molecular and Cellular Biology* (1990) vol. 10 No. 12 (1990) pp. 6482-6490.*
Chemical Abstracts Registry entry 85305-88-0, "Galactosylceramide" entered on Nov 16, 1994.*
Chang et al. "Sustained Expansion of NKT Cells and Antigen-Specific T Cells After Injection of α-Galactosyl-Ceramide Loaded Mature Dendritic Cells in Cancer Patients" *The Journal of Experimental Medicine* 201(9):1503-1517 (2005).
Giaccone et al. "A Phase I Study of the Natural Killer T-Cell Ligand α-Galactosylceramide (KRN7000) in Patients with Solid Tumors" *Clinical Cancer Research* 3702(8):3702-3709 (2002).
Ishikawa et al. "A Phase I Study of α-Galactosylceramide (KRN7000)-Pulsed Dendritic Cells in Patients with Advanced and Recurrent Non-Small Cell Lung Cancer" *Clinical Cancer Research* 1910(11):1910-1917 (2005).
Matsuyoshi et al. "Therapeutic Effect of α-Galactosylceramide-Loaded Dendritic Cells Genetically Engineered to Express SLC/CCL21 Along with Tumor Antigen Against Peritoneally Disseminated Tumor Cells" *Cancer Sci* 96(12):889-896 (2005).
Nagaraj et al. "Dendritic Cells Pulsed with Alpha-Galactosylceramide Induce Anti-Tumor Immunity Against Pancreatic Cancer in vivo" *International Immunology* 18(8):1279-1283 (2006).
Nicol et al. "Human Invariant Vα24+ Natural Killer T Cells Activated by α-Galactosylceramide (KRN7000) Have Cytotoxic Anti-Tumour Activity Through Mechanisms Distinct from T Cells and Natural Killer Cells" *Immunology* 99:229-234 (2000).
Rusyn et al. "CLN3p Impacts Galactosylceramide Transport, Raft Morphology, and Lipid Content" *Pediatric Research* 63(6):625-631 (2008).
Stagg et al. "From Cancer Immunosurveillance to Cancer Immunotherapy" *Immunological Reviews* 220:82-101 (2007).
Sullivan and Kronenberg. "Activation or Anergy: NKT Cells are Stunned by α-Galactosylceramide" *The Journal of Clinical Investigation* 115(9):2328-2329 (2005).
Zaini et al. "OX40 Ligand Expressed by DCs Costiumlates NKT and CD4+ Th Cell Antitumor Immunity in Mice" *The Journal of Clinical Investigations* 117(11):3330-3338 (2007).
Boustany and Kolodny. "Neurological Process. The Neuronal Ceroid Liposuscinoses: A Review" *Rev Neurol* (Paris) 145(2):105-110 (Abstract only), (1989).
Boustany et al. "Clinical Classification of Neuronal Ceroid-Lipofuscinosis Subtypes" *American Journal of Medical Genetics Supplement* 5:47-58 (1988).
Dhar et al. "Flupirtine Blocks Apoptosis in Batten Patient Lymphoblasts and in Human Postmitotic CLN3- and CLN2-Deficient Neurons" *Ann Neurol* 51:448-466 (2002).
Gao et al. "Mutations in a Novel *CLN6*-Encoded.Transmembrane Protein Cause Variant Neuronal Ceroid Lipofuscinosis in Man and Mouse" *Am J Hum Genet* 70:324-335 (2002).
Guo et al. "A Disrupted Homologue of the Human *CLN3* or Juvenile Neuronal Ceroid Lipofuscinosis Gene in *Saccharomyces cerevisiae*: A Model to Study Batten Disease" *Cellular and Molecular Neurobiology* 19(5):671-680 (1999).

(Continued)

Primary Examiner — Eric S Olson
(74) Attorney, Agent, or Firm — Myers Bigel Sibley & Sajovec, P.A.

(57) ABSTRACT

The present invention provides methods and compositions for treating a disorder associated with a deficiency in a gene product of a CLN gene in a subject (e.g., neuronal ceroid lipofuscinosis (NCL)), comprising administering to the subject an effective amount of a sphingolipid (e.g., galactosylceramide, ceramide, lysophosphatidic acid, sulfatide and any combination thereof), thereby treating the disorder in the subject.

17 Claims, 11 Drawing Sheets

OTHER PUBLICATIONS

Haines et al. "Chromosomal Localization of Two Genes Underlying Late-Infantile Neuronal Ceroid Lipofuscinosis" *Neurogenetics* 1:217-222 (1998).

Haines et al. "Genome-Wide Search for *CLN2*, the Gene Causing Late-Infantile Neuronal Ceroid-Lipofuscinosis (LNCL)" *American Journal of Medical Genetics* 57:344-347 (1995).

Haines et al. "Linkage Analysis in Juvenile Neuronal Ceroid Lipofuscinosis" *American Journal of Medical Genetics* 42:542-545 (1992).

Lerner et al. "Linkage Disequlibrium Between the Juvenile Neuronal Ceroid Lipofuscinosis Gene and Marker Loci on Chromosome 16p12.1" *Am J Hum Genet* 54:88-94 (1994).

Munroe et al. "Spectrum of Mutations in the Batten Disease Gene, *CLN3*" *Am J Hum Genet* 61:310-316 (1997).

Pane et al. "Expression of CLN3 in Human NT2 Neuronal Precursor Cells and Neonatal Rat Brain" *Pediatric Research* 46(4):367-374 (1999).

Persaud-Sawin and Boustany. "Cell Death Pathways in Juvenile Batten Disease" *Apoptosis* 10(5):973-985 (2005).

Persaud-Sawin et al. "A Galactosylceramide Binding Domain is Involved in Trafficking of CLN3 from Golgi to Rafts via Recycling Endosomes" *Pediatric Research* 56(3):449-463 (2004).

Persaud-Sawin et al. "Motifs Within the CLN3 Protein: Modulation of Cell Growth Rates and Apoptosis" *Human Molecular Genetics* 11(18):2129-2142 (2002).

Persaud-Sawin et al. "Neuronal Ceroid Lipofuscinosis: A Common Pathway?" *Pediatric Research* 61(2):146-152 (2007).

Puranam et al. "CLN3 Defines a Novel Antiapoptotic Pathway Operative in Neurodegeneration and Mediated by Ceramide" *Mol Genet Metab* 66(4):294-308 (1999) (Abstract only).

Rakheja et al. "Juvenile Neuronal Ceroid-Lipofuscinosis (Batten Disease): A Brief Review and Update" *Current Molecular Medicine* 7:603-608 (2007).

Rylova et al. "The *CLN3* Gene is a Novel Molecular Target for Cancer Drug Discovery" *Cancer Research* 62:801-808 (2002).

Schulz et al. "The CLN9 Protein, a Regulator of Dihydroceramide Synthase" *The Journal of Biological Chemistry* 281(5):2784-2794 (2006).

Schulz et al. "Impaired Cell Adhesion and Apoptosis in a Novel CLN9 Batten Disease Variant" *Ann Neurol* 56:342-350 (2004).

Sleat et al. "Mutational Analysis of the Defective Protease in Classic Late-Infantile Neuronal Ceroid Lipofuscinosis, a Neurodegenerative Lysosomal Storage Disorder" *Am J Hum Genet* 64:1511-1523 (1999).

Teixeira et al. "Clinicopathological and Molecular Characterization of Neuronal Ceroid Lipofuscinosis in the Portuguese Population" *J Neurol* 250:661-667 (2003).

Teixeira et al. "Gene Expression Profiling in vLINCL CLN6-Deficient Fibroblasts: Insights into Pathobiology" *Biochimica et Biophysica Acta* 1762:637-646 (2006).

Teixeira et al. "Novel Mutations in the CLN6 Gene Causing a Variant Late Infantile Neuronal Ceroid Lipofuscinosis" *Human Mutation* 21:502-508 (2003).

Yan et al. "Localization of Juvenile, but Not Late-Infantile, Neuronal Ceroid Lipofuscinosis on Chromosome 16" *Am J Hum Genet* 52:89-95 (1993).

\* cited by examiner

METHODS AND COMPOSITIONS FOR TREATING DISORDERS CAUSED BY A DEFICIENCY IN A GENE PRODUCT OF A CLN GENE

STATEMENT OF PRIORITY

This application claims the benefit, under 35 U.S.C. §119 (e), of U.S. Provisional Application No. 61/113,676, filed Nov. 12, 2008 and U.S. Provisional Application No. 61/116, 481, filed Nov. 20, 2008, the entire contents of each of which are incorporated by reference herein.

STATEMENT OF GOVERNMENT SUPPORT

Aspects of this invention were supported by funding provided under NINDS Grant No. N0433344. The U.S. Government has certain rights to this invention.

FIELD OF THE INVENTION

The present invention provides methods and compositions for treating disorders caused by a deficiency in the gene product of a CLN gene in a subject.

BACKGROUND OF THE INVENTION

The neuronal ceroid lipofuscinoses (NCL)/Batten disorders are a group of closely related hereditary neurodegenerative disorders that affect infants, children and adults, and which occur at a frequency of between 2 and 4 in 100,000 live births. Most forms of NCL afflict children and their early symptoms and disease progression tend to be similar. Initial diagnosis is frequently based upon visual problems (e.g., retinitis pigmentosa), behavioral changes, mental and motor decline and seizures (1). Progression is reflected by a decline in mental abilities, increasingly severe and untreatable seizures, blindness and loss of motor skills while further progression can result in dementia or a vegetative state. The pathologic hallmark of NCL is neuronal loss. Theories pertaining to pathophysiology include increased lipid peroxidation, alterations in dolichol turnover, increased inflammatory responses, unexplained accumulation and processing of subunit c of mitochondrial ATP synthase, and accelerated apoptosis (2, 3). There is no effective treatment for NCL and all childhood forms are eventually fatal. Several forms of NCL are differentiated according to age of onset, clinical pathology and genetic linkage. These include early infantile NCL (INCL, CLN1), late infantile NCL (LINCL, CLN2), juvenile NCL (JNCL, CLN3) adult NCL (CLN4), two variant forms of LINCL (CLN5 and CLN6) and possibly other atypical forms.

Juvenile neuronal ceroid lipofuscinosis (JNCL), the most common form of NCL, is due to mutations in the CLN3 gene (4). More than 35 mutations are known, most due to a 1.02 kb deletion in genomic DNA, which produces a premature stop codon and loss of nucleotides 461-677. This results in a truncated protein 181 amino acids in length. The CLN3 protein (CLN3p) has four potential glycosylation sites, 12 phosphorylation sites and a farnesylation site. The CLN3 protein imparts anti-apoptotic properties to cells and neurons. Two conserved amino acid stretches within exons 11 and 13, and two of the CLN3p glycosylation sites are necessary for preservation of this function (5). Membrane topology studies suggest that the CLN3p has five transmembrane domains with an extracellular/intraluminal amino-terminus and a cytoplasmic carboxy terminus (6).

CLN3p is highly conserved in eukaryotes and is ubiquitously expressed in mammals. CLN3p imparts anti-apoptotic properties to neurons and other cells (7-9) and regulates autophagy (10). CLN3-deficient cells grow slowly, have enhanced sensitivity to apoptosis and altered levels of ceramide and sphingomyelin. These deficits can be corrected following restoration of CLN3p to CLN3-deficient cells. Additionally, CLN3 mRNA and protein levels are over-expressed in cancer cells (12).

A comprehensive localization study has demonstrated that wild type CLN3p is localized to Golgi apparatus and plasma membranes and traffics via early recycling RAB4- and Rab11-positive endosomes from the Golgi apparatus to lipid rafts (LR) (20). This was established in primary rat hippocampal neurons, post-mitotic human neurons and normal human fibroblasts. Mutant CLN3p localizes to a disrupted Golgi apparatus, fails to reach the plasma membrane and partially mis-localizes to lysosomes.

CLN3p harbors a conserved motif, 291VYFAE295, necessary for its impact on cell growth and apoptosis (20). This motif is embedded in a stretch of amino acids structurally homologous to a GalCer lipid raft binding domain. This domain (21) defines a lipid raft binding site that is structurally identical to the one in prionic protein, PrP and the V3 loop of the HIV-1 surface envelope glycoprotein, gp120. Dual immuno-labeling studies localized wild-type CLN3p with alkaline phosphatase and caveolin-1 to lipid rafts and caveolae in some cell types (20). There was minimal co-localization of mutant CLN3p with these lipid raft markers.

Lipid rafts are involved in multiple cellular processes, including protein trafficking, signaling complex formation and signal transduction events pertinent to apoptosis, cell adhesion (22), stress responses, regulation of the cytoskeleton, conduction of proathrogenic stimuli and immune cell function (21-24). They also serve as portals of entry for toxins, viruses and bacteria (26, 29, 30). Additionally, lipid rafts are important for normal synapse density and morphology in the central nervous system (31), myelin integrity and myelin-axonal interactions (21). Lipid rafts are liquid-ordered microdomains of plasma membrane that are insoluble in non-ionic detergents. These domains are thought to derive from the Golgi apparatus and are made up of glycosphingolipids and cholesterol and are enriched in glycosylphosphatidylinositol (GPI)-anchored proteins (32). They also harbor the sphingolipid, ceramide, a pro-apoptotic lipid second messenger (33, 34). Protein prenylation promotes association of proteins to lipid rafts and CLN3p is prenylated (35). Lipid rafts house caspase-8, the first initiator caspase to be activated in the apoptotic cascade in CLN3-deficient cells (36). Morphologically, in CLN3p-deficient cells, raft vesicular structures are small compared to those derived from normal cells as demonstrated by transmission electron microscopy (TEM). These structural differences may reflect altered sphingolipid composition of CLN3-deficient lipid rafts.

The present invention overcomes previous shortcomings in the art by providing methods and compositions to treat disorders associated with a deficiency in a gene product of a CLN gene (e.g., CLN1, CLN2, CLN3, CLN5, CLN6, CLN7, CLN8, CLN9 or CLN10/CTSD and/or CLCN6).

SUMMARY OF THE INVENTION

The present invention provides methods for treating a disorder (e.g., neuronal ceroid lipofuscinosis (NCL)), associated with a deficiency in a gene product of a CLN gene in a subject, comprising administering to the subject an effective amount of a sphingolipid (e.g., galactosylceramide, ceramide, lysophosphatidic acid, sulfatide and any combination thereof), thereby treating the disorder in the subject.

Further aspects of the invention include a method of treating neuronal ceroid lipofuscinosis (NCL) in a subject, comprising administering an effective amount of a sphingolipid of this invention to the subject, thereby treating NCL in the subject. In some embodiments, the NCL is juvenile NCL (JNCL).

Also included in the present invention is a method of treating a disorder (e.g., neuronal ceroid lipofuscinosis (NCL)), associated with a deficiency in a gene product of a CLN gene in a subject, comprising administering to the subject a heterologous nucleic acid comprising a heterologous nucleotide sequence encoding an enzyme in the synthetic pathway of a sphingolipid of this invention (e.g., galactosylceramide synthase), thereby treating the disorder in the subject.

In further embodiments, the present invention provides a method of reducing apoptosis in a subject, wherein the apoptosis is due to or results from a deficiency in a gene product of a CLN gene, comprising administering to the subject an effective amount of a sphingolipid of this invention (e.g., galactosylceramide) and/or a heterologous nucleic acid comprising a heterologous nucleotide sequence encoding an enzyme in the synthetic pathway of a sphingolipid of this invention, thereby reducing apoptosis due to a deficiency in a gene product of a CLN gene in the subject.

Additional aspects of this invention include a method of correcting aberrant ultrastructural morphology of a cell in a subject, wherein the aberrant ultrastructural morphology is due to or results from a deficiency in a gene product of a CLN gene, comprising administering to the subject an effective amount of a sphingolipid of this invention (e.g., galactosylceramide) and/or a heterologous nucleic acid comprising a heterologous nucleotide sequence encoding an enzyme in the synthetic pathway of a sphingolipid of this invention, thereby correcting aberrant ultrastructural morphology of the cell in the subject.

Also provided herein is a method of correcting aberrant lipid stoichiometry of lipid rafts in a cell of a subject, wherein the aberrant lipid stoichiometry of lipid rafts is due to or results from a deficiency in a gene product of a CLN gene, comprising administering to the subject an effective amount of a sphingolipid of this invention (e.g., galactosylceramide) and/or a heterologous nucleic acid comprising a heterologous nucleotide sequence encoding an enzyme in the synthetic pathway of a sphingolipid of this invention, thereby correcting aberrant lipid stoichiometry of lipid rafts in the cell of the subject.

DETAILED DESCRIPTION OF THE INVENTION

Figure 1:
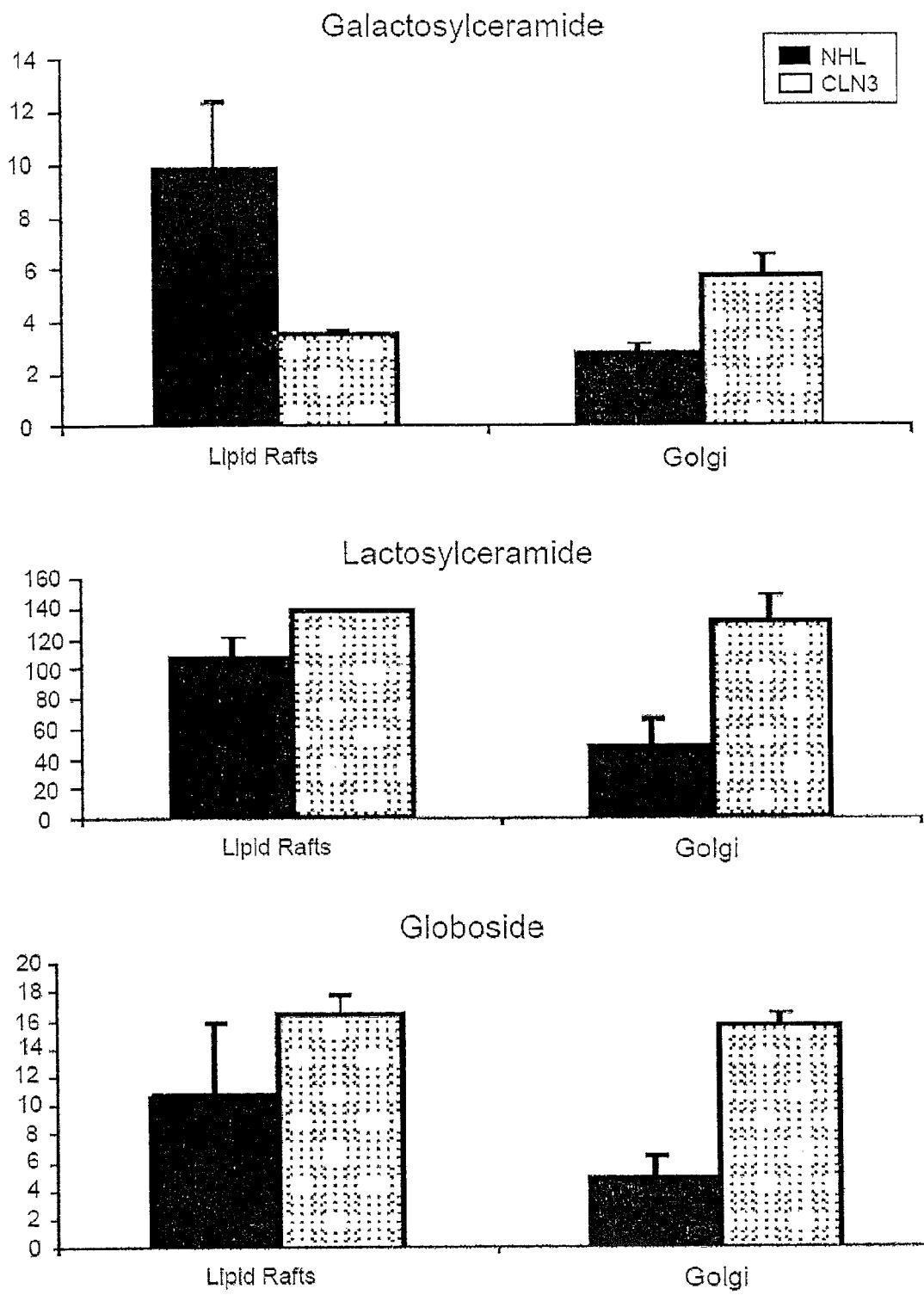
FIG. 1. Galactose labeling of CLN3-deficient cells. NhL: normal human lymphoblasts; CLN3(−): CLN3-deficient cells. Black bars: normal cell lipid values; spotted bars: CLN3-deficient cell values. Top panel: de novo GalCer; middle panel: de novo LacCer; bottom panel: de novo globoside. De novo GalCer raft/Golgi ratio reverses in CLN3-deficient cells. More GalCer reaches lipid rafts in normal cells. De novo synthesized LacCer and globoside are elevated in rafts and Golgi or CLN3-deficient cells compared to normal. Lipids were normalized to protein content. The data represent three separate experiments.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

The present invention is based on the unexpected discovery that a sphingolipid (e.g., galactosylceramide (GALCER)) can be administered to a subject having or at risk of having a disorder associated with or caused by a deficiency in a gene product of a CLN gene. Thus, the present invention provides a method for treating a disorder (e.g., neuronal ceroid lipofuscinosis (NCL)), associated with or caused by a deficiency in a gene product of a CLN gene in a subject, comprising administering to the subject an effective amount of a sphingolipid, thereby treating the disorder in the subject.

The present invention further provides a method of treating neuronal ceroid lipofuscinosis (NCL) in a subject, comprising administering an effective amount of a sphingolipid to the subject, thereby treating NCL in the subject. A nonlimiting example of a NCL that can be treated according to methods of this invention is juvenile NCL (JNCL). Other disorders associated with or caused by a deficiency in a gene product of a CLN gene include but are not limited to early infantile NCL (INCL, CLN1), late infantile NCL (LINCL, CLN2), juvenile NCL (JNCL, CLN3) adult NCL (CLN4), variant forms of LINCL (CLN5 and CLN6), Batten disease, disorders associated with defects in CLN8 and/or CLN9, congenital NCL (CLN10) and other atypical forms of NCL now known or later identified. In some embodiments of this invention, one or more than one disorder associated with or caused by a deficiency in a gene product of a CLN gene can be excluded from the list of disorders of this invention.

A CLN gene of this invention includes but is not limited to CLN1, CLN2, CLN3, CLN5, CLN6, CLN7, CLN8, CLN9 or CLN10/CTSD and CLCN6 in any combination. In some embodiments of this invention, one or more than one CLN gene in any combination can be excluded from the list of CLN genes of this invention A deficiency in a gene product of a CLN gene of this invention can be due to a mutation or other genetic alteration (e.g., deletion, addition, rearrangement, substitution, etc.) that results in a decrease or deficiency in the amount and/or activity of the gene product of the CLN gene. A decrease or deficiency in the amount and/or activity of the gene product of a CLN gene can be determined by one of ordinary skill in the art employing standard methods. For CLN1, CLN2 and CLN10, measurement of the enzyme activities of protein palmitoyl thioesterase, tripeptidypeptidase and cathepsin D, respectively, can be carried out to provide a diagnosis. For CLN3, CLN5, CLN6, CLN7 and CLN8, amplification-based technologies (e.g., polymerase chain reaction (PCR), or gene sequencing can be carried out to provide a diagnosis (Boustany and Zucker (2006): "Degenerative diseases primarily of grey matter" in *Pediatric Neurology Principles and Practice* K E Swaiman, S Ashwal, D Ferriero, eds. Vol 2:1313).

A sphingolipid of this invention includes a lipid comprising a sphingosine backbone that is O-linked to a charged head group or a hydrogen ion (in ceramide), phosphocholine (in sphingomyelin), ethanolamine, serine, or choline. The backbone is also amide-linked to an acyl group, such as a fatty acid. Ceramide is the fundamental structural unit common to all sphingolipids, consisting of a fatty acid chain attached through an amide linkage to sphingosine.

Nonlimiting examples of a sphingolipid of this invention include galactosylceramide, ceramide, sphingomyelins, glycosphingolipids, cerebrosides, lysophosphatidic acid, sulfatide, and other sphingolipids now known or later identified, as well as active domains thereof and including any combination thereof and in any ratio relative to one another. In some embodiments of this invention, one or more than one sphingolipid in any combination can be excluded from the list of sphingolipids of this invention. In some embodiments, the sphingolipid of this invention can be D-Galactosyl-β1-1' Ceramide (C12), available from Avanti Polar Lipids, Inc. (Alabaster, Ala.), or KRN7000 (Kirin Brewery, Japan). Other sphingolipids available, e.g., from Avanti Polar Lipids, Inc. include D-Glucosyl-β1-1' Ceramide (C8), D-Galactosyl-β1-1' Ceramide (C8), D-Lactosyl-β1-1' Ceramide (C8), D-Glucosyl-β1'-1' Ceramide (C12), D-Galactosyl-β1-1' Ceramide (C12), D-Lactosyl-β1-1' Ceramide (C12), 1,2-Dioleoyl-sn-Glycero-3-Phosphoethanolamine-N-Lactose, Sphingomyelin, other ceramides, cerebrosides, brain sulfatides and the like, in any combination, as would be well known in the art.

The present invention further provides a method of treating a disorder (e.g., neuronal ceroid lipofuscinosis (NCL)), associated with or caused by a deficiency in a gene product of a CLN gene in a subject, comprising administering to the subject a heterologous nucleic acid comprising a nucleotide sequence encoding an enzyme (or any combination of enzymes) in the synthetic pathway of a sphingolipid of this invention (e.g., galactosylceramide synthase), thereby treating the disorder in the subject. Enzymes in the synthetic pathway of a variety of sphingolipids are well known in the art and include, without limitation, galactosylceramide synthase, serine palmitoyltransferase, NADPH-dependent reductase, dihydroceramide synthase, dihydroceramide desaturase, sphingomyelin synthase, sphingomyelinase, galactosylceramide transferase, glucosylceramide synthase, lactosylceramide synthase, galacyocerebrosidase, beta glucosidase, GB3/CD77 synthase, alpha galactosidase and any other enzyme in the sphingolipid synthetic pathway now known or later identified. The nucleotide sequence and amino acid sequence of the enzymes of the synthetic pathway of a sphingolipid are available in the art (e.g., from sequence databases such as the GenBank® database) and are incorporated by reference herein in their entireties.

The introduction of a heterologous nucleic acid comprising a heterologous nucleotide sequence encoding an enzyme of this invention into a cell of a subject of this invention is carried out by methods routine in the art. The heterologous nucleotide sequence is expressed in the cell, thereby producing the encoded enzyme, the presence of which corrects the defect in the cell caused by the deficiency in the gene product of the CLN gene.

Further embodiments of this invention include a method of reducing apoptosis of cells (e.g., neuronal cells) in a subject, wherein the apoptosis is due to or results from a deficiency in a gene product of a CLN gene, comprising administering to the subject an effective amount of a sphingolipid of this invention (e.g., galactosylceramide) and/or a heterologous nucleic acid comprising a heterologous nucleotide sequence encoding an enzyme (or a combination of enzymes) in the synthetic pathway of a sphingolipid of this invention, thereby reducing apoptosis of cells in the subject. By "reducing apoptosis" according to the methods of this invention is meant that abnormal or aberrant apoptosis that is due to or results from the deficiency in the gene product of the CLN gene is lessened or reduced. In other words, the rate and/or degree of apoptosis that is due to or results from the deficiency in the gene product of the CLN gene is lessened or reduced, as compared to the rate and/or degree of apoptosis in a subject that has not been administered an effective amount of a sphingolipid and/or a heterologous nucleotide sequence encoding an enzyme in the synthetic pathway of a sphingolipid of this invention. Methods of determining a rate or degree of apoptosis are well known in the art and thus one of ordinary skill would be able to determine whether the rate and/or degree of apoptosis is lessened or reduced upon carrying out the methods of treatment described in this invention. The rate and/or degree of apoptosis can be determined according to methods well known in the art, such as by comparing the growth rate of patient-derived lymphoblasts or fibroblasts with controls and by propidium iodide staining of such cells before and after treatment according to the methods of this invention.

A method is also provided herein of correcting aberrant or abnormal ultrastructural morphology of a cell (e.g., a neuronal cell, fibroblast and/or lymphoblast) in a subject, wherein the aberrant or abnormal ultrastructural morphology of the cell is due to or results from a deficiency in a gene product of a CLN gene, comprising administering to the subject an effective amount of a sphingolipid of this invention (e.g., galactosylceramide) and/or a heterologous nucleic acid comprising a heterologous nucleotide sequence encoding an enzyme in the synthetic pathway of a sphingolipid of this invention, thereby correcting aberrant ultrastructural morphology of the cell in the subject. By "correcting aberrant or abnormal ultrastructural morphology" according to the methods of this invention is meant that abnormal or aberrant ultrastructural morphology that is due to or results from the deficiency in the gene product of the CLN gene is corrected (e.g., lessened or reduced). In other words, the type and/or degree of aberrant or abnormal ultrastructural morphology that is due to or results from the deficiency in the gene product of the CLN gene is corrected (e.g., lessened or reduced), as compared to the type and/or degree of aberrant or abnormal ultrastructural morphology in a subject that has not been administered an effective amount of a sphingolipid and/or a heterologous nucleotide sequence encoding an enzyme in the synthetic pathway of a sphingolipid of this invention. Methods of determining a type and/or degree of aberrant or abnormal ultrastructural morphology are well known in the art and thus one of ordinary skill would be able to determine whether the type and/or degree of aberrant or abnormal ultrastructural morphology is corrected (e.g., lessened or reduced) upon carrying out the methods of treatment described in this invention. A determination of whether the type and/or degree of aberrant or abnormal ultrastructural morphology is corrected can be made according to methods well known in the art, such as by employing transmission electron microscopy (TEM) protocols to observe and/or evaluate the ultrastructural morphology of treated cells, untreated cells and control cells.

Additionally, provided herein is a method of correcting aberrant or abnormal lipid stoichiometry of lipid rafts in a cell of a subject, wherein the aberrant or abnormal lipid stoichiometry of lipid rafts in the cell is due to or results from a deficiency in a gene product of a CLN gene, comprising administering to the subject an effective amount of a sphingolipid of this invention (e.g., galactosylceramide) and/or a heterologous nucleic acid comprising a heterologous nucleotide sequence encoding an enzyme in the synthetic pathway of a sphingolipid of this invention, thereby correcting aberrant lipid stoichiometry of lipid rafts in the cell of the subject. By "correcting aberrant or abnormal lipid stoichiometry of lipid rafts" according to the methods of this invention is meant that abnormal or aberrant lipid stoichiometry of lipid rafts that is due to or results from the deficiency in the gene product of the CLN gene is corrected (e.g., lessened or reduced). In other words, the type and/or degree of aberrant or abnormal lipid stoichiometry of lipid rafts that is due to or results from the deficiency in the gene product of the CLN gene is corrected (e.g., lessened or reduced), as compared to the type and/or degree of aberrant or abnormal lipid stoichiometry of lipid rafts in a cell of a subject that has not been administered an effective amount of a sphingolipid and/or a heterologous nucleotide sequence encoding an enzyme in the synthetic pathway of a sphingolipid of this invention. Methods of determining a type and/or degree of aberrant or abnormal lipid stoichiometry of lipid rafts are well known in the art and thus one of ordinary skill would be able to determine whether the type and/or degree of aberrant or abnormal lipid stoichiometry of lipid rafts is corrected (e.g., lessened or reduced) upon carrying out the methods of treatment described in this invention. Such determinations can be carried, for example, by fractionating cells by differential ultracentrifugation, collecting the lipid raft fractions, determining the amount of sphingolipids and glycosphingolipids in the fractions and comparing the amount to the amount of sphingolipids and glycosphingolipids of lipid raft fractions from normal cells.

The terms "exogenous" and/or "heterologous" as used herein can include a nucleotide sequence that is not naturally occurring in the nucleic acid construct and/or delivery vector (e.g., virus delivery vector) in which it is contained and can also include a nucleotide sequence that is placed into a non-naturally occurring environment and/or position relative to other nucleotide sequences (e.g., by association with a promoter or coding sequence with which it is not naturally associated). A heterologous or exogenous nucleotide sequence or amino acid sequence of this invention can be any heterologous nucleotide sequence and/or amino acid sequence that has been introduced into a cell and can include a nucleotide sequence and/or amino acid sequence for which an original version is already present in the cell and the heterologous nucleotide sequence and/or amino acid sequence is a duplicate of the original naturally occurring version, and/or the heterologous nucleotide sequence or amino acid sequence can be introduced into a cell that does not naturally comprise the same nucleotide sequence and/or amino acid sequence.

The nucleic acid of this invention can be present in a vector and such a vector can be present in a cell. Any suitable vector is encompassed in the embodiments of this invention, including, but not limited to, nonviral vectors (e.g., plasmids, poloxymers and liposomes), viral vectors and synthetic biological nanoparticles (BNP) (e.g., synthetically designed from different adeno-associated viruses, as well as other parvoviruses).

It will be apparent to those skilled in the art that any suitable vector can be used to deliver a heterologous nucleic acid of this invention. The choice of delivery vector can be made based on a number of factors known in the art, including age and species of the target host, in vitro vs. in vivo delivery, level and persistence of expression desired, intended purpose (e.g., for therapy or polypeptide production), the target cell or organ, route of delivery, size of the isolated nucleic acid, safety concerns, and the like.

Suitable vectors also include virus vectors (e.g., retrovirus, alphavirus; vaccinia virus; adenovirus, adeno-associated virus, or herpes simplex virus), lipid vectors, poly-lysine vectors, synthetic polyamino polymer vectors that are used with nucleic acid molecules, such as plasmids, and the like.

Any viral vector that is known in the art can be used in the present invention. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Geminivirus; Group Giardiavirus; Hepadnaviridae; Herpesviridae; Hordeivirus virus group; Illarvirus virus group; lnoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and Plant virus satellites.

Protocols for producing recombinant viral vectors and for using viral vectors for nucleic acid delivery can be found, e.g., in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

Nonlimiting examples of vectors employed in the methods of this invention include any nucleotide construct used to deliver nucleic acid into cells, e.g., a plasmid, a nonviral vector or a viral vector, such as a retroviral vector which can package a recombinant retroviral genome (see e.g., Pastan et al., *Proc. Natl. Acad. Sci. U.S.A.* 85:4486 (1988); Miller et al., *Mol. Cell. Biol.* 6:2895 (1986)). For example, the recombinant retrovirus can then be used to infect and thereby deliver a nucleic acid of the invention to the infected cells. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naldini et al., *Science* 272:263-267, 1996), pseudotyped retroviral vectors (Agrawal et al., *Exper. Hematol.* 24:738-747, 1996), and any other vector system now known or later identified. Also included are chimeric viral particles, which are well known in the art and which can comprise viral proteins and/or nucleic acids from two or more different viruses in any combination to produce a functional viral vector. Chimeric viral particles of this invention can also comprise amino acid and/or nucleotide sequence of non-viral origin (e.g., to facilitate targeting of vectors to specific cells or tissues and/or to induce a specific immune response). The present invention also provides "targeted" virus particles (e.g., a parvovirus vector comprising a parvovirus capsid and a recombinant AAV genome, wherein an exogenous targeting sequence has been inserted or substituted into the parvovirus capsid).

Physical transduction techniques can also be used, such as liposome delivery and receptor-mediated and other endocytosis mechanisms (see, for example, Schwartzenberger et al., *Blood* 87:472-478, 1996). This invention can be used in conjunction with any of these and/or other commonly used nucleic acid transfer methods. Appropriate means for transfection, including viral vectors, chemical transfectants, or physico-mechanical methods such as electroporation and direct diffusion of DNA, are described by, for example, Wolff et al., *Science* 247:1465-1468, (1990); and Wolff, *Nature* 352:815-818, (1991).

Thus, administration of the nucleic acid of this invention can be achieved by any one of numerous, well-known approaches, for example, but not limited to, direct transfer of the nucleic acids, in a plasmid or viral vector, or via transfer in cells or in combination with carriers such as cationic liposomes. Such methods are well known in the art and readily adaptable for use in the methods described herein. Furthermore, these methods can be used to target certain diseases and tissues, organs and/or cell types and/or populations by using the targeting characteristics of the carrier, which would be well known to the skilled artisan. It would also be well understood that cell and tissue specific promoters can be employed in the nucleic acids of this invention to target specific tissues and cells and/or to treat specific diseases and disorders.

An effective amount of a composition of this invention will vary from composition to composition and subject to subject, and will depend upon a variety of factors such as age, species, gender, weight, overall condition of the subject and the particular disease or disorder to be treated. An effective amount can be determined in accordance with routine pharmacological procedures known to those of ordinary skill in the art. In some embodiments, a dose ranging from about 0.1 µg/kg to about 1 gm/kg will have therapeutic efficacy. In embodiments employing viral vectors for delivery of the nucleic acid of this invention, viral doses can be measured to include a particular number of virus particles or plaque forming units (pfu) or infectious particles, depending on the virus employed. For example, in some embodiments, particular unit doses can include about $10^3$, $10^4$, $10^5$, $10^6$, $10^7$, $10^8$, $10^9$, $10^{10}$, $10^{11}$, $10^{12}$, $10^{13}$ or $10^{14}$ pfu or infectious particles.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year and/or as necessary to control a particular condition and/or to achieve a particular effect and/or benefit. In some embodiments, one, two, three or four doses over the lifetime of a subject can be adequate to achieve the desired therapeutic effect. The amount and frequency of administration of the composition of this invention will vary depending on the particular condition being treated or to be prevented and the desired therapeutic effect.

The term "isolated" as used herein means a sphingolipid or active fragment or domain thereof or a nucleic acid or cell of this invention that is sufficiently free of contaminants or cell components or other biological components with which sphingolipids and/or nucleic acids and/or cells normally occur. "Isolated" does not mean that the preparation is technically pure (homogeneous), but it is sufficiently pure to provide the sphingolipid or nucleic acid or cell in a form in which it can be used therapeutically. Furthermore, an isolated cell is a cell that has been separated from other components with which it is normally associated in nature. For example, an isolated cell can be a cell in culture medium and/or a cell in a pharmaceutically acceptable carrier of this invention.

A cell of this invention can be any cell that can express a nucleotide sequence encoding a gene product of a CLN gene. Such a cell can be in vitro, ex vivo and/or in vivo. Nonlimiting examples of a cell of this invention include neuronal precursor cells, fibroblasts, lymphoblasts, stem cells and any combination thereof.

A cell of this invention, including an isolated cell, can be a cell in a subject of this invention. A subject of this invention can be any animal that can produce a gene product of a CLN gene. Nonlimiting examples of a subject of this invention include mammals such as humans, mice, dogs, cats, horses, cows, rabbits, goats and sheep, etc. A subject of this invention can also be a subject in need of a method of this invention as provided herein (e.g., a subject diagnosed with or suspected of having a disorder associated with or caused by a deficiency in a gene product of a CLN gene, as well as a subject at risk of developing a disorder associated with or caused by a deficiency in a gene product of a CLN gene (e.g., a subject in whom a mutation or genetic alteration in a CLN gene has been identified and/or in whom a family history of a disorder associated with or caused by a deficiency in a gene product of a CLN gene has been identified). Thus, the methods of this invention can in some embodiments be employed prophylactically or preventatively to prevent or delay the onset and/or progression of a disorder associated with or caused by a deficiency in a gene product of a CLN gene.

"Treat," "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay in the progression of the condition, prevention or delay of the onset of the disorder, and/or change in clinical parameters, disease or illness, etc., as would be well known in the art.

As used herein, "effective amount" refers to an amount of a compound or composition of this invention that is sufficient to produce a desired effect, which can be a therapeutic effect. The effective amount will vary with the age, general condition of the subject, weight of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

The present invention further provides a composition (e.g., a pharmaceutical composition) comprising a sphingolipid of this invention, either alone and/or in any combination with other sphingolipids and/or one or more therapeutic reagents such as flupirtine, other known neuroprotective anti-apoptotic agents, anti-inflammatory drugs and/or immunosuppressants and these compositions can be present in a pharmaceutically acceptable carrier. In some embodiments, a combination of lysophosphatidic acid plus GALCER and/or sulfatide and/or ceramide can be employed in the methods and compositions of this invention. The compositions described herein can be formulated for administration in a pharmaceutical carrier in accordance with known techniques. See, e.g., Remington, *The Science And Practice of Pharmacy* (latest edition). By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents. In certain embodiments, the pharmaceutically acceptable carrier is sterile and would be deemed suitable for administration into human subjects according to regulatory guidelines for pharmaceutical compositions comprising the carrier.

The pharmaceutical compositions of this invention include those suitable for administration to subjects of this invention, including subjects in need thereof. As used herein, administer or administration refers to oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 0.1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

An effective amount of a composition of this invention, the use of which is in the scope of present invention, will vary from composition to composition, and subject to subject, and will depend upon a variety of well known factors such as the age and condition of the patient and the form of the composition and route of delivery. An effective amount can be determined in accordance with routine pharmacological procedures known to those skilled in the art.

As a general proposition, a dosage from about 0.01 μg/kg to about 50 mg/kg (e.g., 0.01 μg/kg. 0.1 μg/kg, 1 μg/kg, 5 μg/kg 10 μg/kg. 25 μg/kg. 50 μg/kg. 75 μg/kg, 100 μg/kg, 200 μg/kg, 500 μg/kg, 1 mg/kg. 10 mg/kg, 20 mg/kg, 30 mg/kg, 40 mg/kg or 50 mg/kg) will have therapeutic efficacy, with all weights being calculated based upon the weight of the composition. In some embodiments, a dosage from about 1.0 μg/kg to about 100 μg/kg would be an effective amount. An effective amount of galactosylceramide can be determined according to methods known in the literature (see, e.g., The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic effect. The amount and frequency of administration of the composition of this invention will vary depending on the particular condition being treated or to be prevented and the desired therapeutic effect.

The compositions of this invention can be administered to a cell of a subject either in vivo or ex vivo. For administration to a cell of the subject in vivo, as well as for administration to the subject, the compositions of this invention can be administered, for example as noted above, orally, parenterally (e.g., intravenously), by intramuscular injection, intradermally (e.g., by gene gun), by intraperitoneal injection, subcutaneous injection, transdermally, extracorporeally, topically or the like.

If ex vivo methods are employed, cells or tissues can be removed and maintained outside the body according to standard protocols well known in the art while the compositions of this invention are introduced into the cells or tissues. For example, a nucleic acid of this invention can be introduced into cells via any gene transfer mechanism, such as, for example, virus-mediated gene delivery, calcium phosphate mediated gene delivery, electroporation, microinjection and/or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

The present invention is more particularly described in the Examples set forth below, which are not intended to be limiting of the embodiments of this invention.

EXAMPLES

Example 1

CLN3 Aids Galactosylceramide Transport to Lipid Rafts and Impacts Raft Stoichiometry and Morphology JNCL is caused by mutations in the CLN3 gene. CLN3 protein (CLN3p) localizes to Golgi/Rab4-/Rab11-positive endosomes and lipid rafts, and has a galactosylceramide (GalCer) lipid raft-binding domain. In CLN3-deficient cells, galactosylceramide and mutant CLN3 protein are retained in the Golgi apparatus, with CLN3p rescuing GalCer deficits in lipid rafts. Reintroduction of CLN3 rescues the galactosylceramide deficit observed n lipid rafts. Wild-type CLN3p directly binds GalCer and sulfatide, the sulfated form of GalCer and also a component of lipid rafts, but mutant CLN3p fails to bind to GalCer or sulfatide. Sphingolipid composition of lipid rafts and Golgi apparatus is perturbed in CLN3-deficient cells. GalCer is decreased in lipid rafts and accumulated in the Golgi complex. Morphologically, CLN3-deficient lipid rafts have smaller vesicular structures than those derived from normal cells as visualized by transmission electron microscopy (TEM), which may reflect altered sphingolipid composition of CLN3-deficient lipid rafts. Additionally, CLN1, CLN2 and CLN6 proteins are shown to bind to lysophosphatidic acid and sulfatide, CLN6 and CLN8 proteins are shown to bind to GalCer, and CLN8 protein is shown to bind to ceramide. The sphingolipid composition and morphology of lipid rafts in CLN1-, CLN2-, CLN6-, CLN8- and CLN9-deficient cells differed from normal, indicating that alterations in lipid raft structure and lipid biochemistry/stoichiometry could be common themes underlying disorders associated with a deficiency in these CLN proteins.

Cell Culture. Lymphoblasts are grown at 37° C. and in 5% $CO_2$ in RPMI 1640 medium (Sigma-Aldrich, St Louis, Mo.)/ 10% fetal bovine serum and 1% antibiotic/antimycotic. Immortalized lymphoblast cell lines originally obtained from JNCL and other NCL patients and normal donors, were used for all experiments. Fibroblasts from normal and mnd (CLN8-deficient) mice were also used. All JNCL lymphoblasts used are homozygous for the 1.02 kb deletion in the genomic DNA.

Reagents/Antibodies. Anti-GRASP65 mouse monoclonals anti-Rab4, anti-Rab7 and anti-Rab11, goat polyclonal anti-alkaline phosphatase and anti-caveolin-1 antibodies were purchased from RDI (Concord, Mass.). FFA BSA was purchased from Sigma. DMEM and FBS were purchased from Invitrogen (Carlsbad, Calif.). Boron dipyrromethene difluoride or BODIPY-GalCer was purchased from Molecular Probes (Eugene, Oreg.). Alexafluor secondary antibody, alexafluor 568 (red) or alexafluor 488 (green) were also purchased from Molecular Probes.

Antibodies previously characterized are rabbit polyclonal anti-CLN3 antibody to residues 58-77 (10,18), sheep polyclonal anti-CLN6 antibody to residues 284-301 and sheep polyclonal anti-CLN8 antibody to residues 2-19, rabbit polyclonal anti-CLN2 antibody (Orbigen Inc., San Diego, Calif.), rabbit polyclonal anti-CLN1 antibody is also previously characterized.

GalCer distribution in fibroblasts. Normal and JNCL fibroblasts were plated on sterile poly-D-Lysine-treated coverslips and grown overnight to 80% confluence in DMEM/10% FBS/ 1% antibiotic at 37° C. and 5% $CO_2$. Cells are incubated with BODIPY-GalCer/FFA-BSA for 2-5 min at 37° C. and 5% $CO_2$ then washed as previously described. Following the acid wash, the cells were rinsed three times in FFA-BSA before being fixed (20). After fixing, the cells were blocked in 5% FFA-BSA for 1 hr at room temperature (RT), incubated with primary antibody for 1 hr at RT, and then washed three times in block solution for 10 minutes at RT. This was repeated two times. The cells were then blocked as before and the secondary Ab was added for 1 hr at RT, washed twice in blocking solution, followed by 3 washes in RT PBS and then mounted onto a slide with 40 µl of Fluoromount G and visualized with a Zeiss LSM 510 confocal microscope (100× magnification).

Protein-lipid overlay assay. Membrane arrays (SPHINGOSTRIPS (Echelon Research Laboratories, Salt Lake City, Utah), or lipids were spotted on nitrocellulose membranes and dried for at least one hour. Membranes were blocked with 3% (wt/vol) Fatty Acid Free or FFA-BSA (Sigma-Aldrich, St. Louis, Mo.) in Tris-Buffered Saline Tween-20 (TBST) [150 mM NaCl/10 mM Tris.HCl (pH 8.0), and 0.1% (vol/vol) Tween-20] for 1 h at RT. Blocked membranes were incubated for 8 h at 4° C. with 2 mg/ml of total cell lysate.

Fibroblasts overexpressing CLN3p (AC1 cells) and JNCL fibroblasts were used for the GalCer-CLN3 binding assay. The membranes were then washed five times for 5 min each with TBST. After washing, membranes were incubated with anti-CLN3, CLN1, CLN2, CLN6 or CLN8-antibodies overnight at 1:1000 dilution, followed by additional washing and incubation with horseradish peroxidase-conjugated anti-rabbit IgG goat antibody for 1 h at RT. After a final washing, enhanced chemiluminescence was used to detect binding of NCL proteins to sphingolipids. Intensity values were computed with an ImageJ software program.

Subcellular fractionation. Lymphoblasts were washed twice with PBS and lysed in 300 microliters (µl) of ice-cold medium (150 mM NaCl, 5 mM dithiothreitol (DTT), 5 mM EDTA, 25 mM Tris-HCl, pH 7.5 supplemented with a cocktail of protease inhibitors and 1% Triton X-100) on ice. Samples were mixed with 300 µl cold 85% sucrose, transferred into SW41Ti centrifuge tubes and overlaid with 35%-0% sucrose. The gradient mixtures were spun at 34,000 rpm in a SW41Ti rotor for 18 h at 4° C. Nine 0.5 ml fractions (top to bottom) were collected. 250 µl of each fraction were used for lipid extraction and TLC analysis and 15 µl of each fraction were used for Western blotting analysis. Equal portions of each fraction were used for the GalCer dot-blot assay.

GalCer dot-blot assay. 0.2 µl of each subcellular fraction was applied on nitrocellulose membrane and dried for one hour. Membranes were blocked with 3% (wt/vol) FFA-BSA in TBST [150 mM NaCl/10 mM Tris.HCl (pH 8.0), and 0.1% (vol/vol) Tween-20] for 1 h at RT. Blocked membranes were incubated for 2 h at RT with rabbit anti-GalCer or anti-GlcCer primary antibody (Sigma-Aldrich; St Louis, Mo.) at 1:1000 dilution, then washed five times for 5 min each with TBST followed by incubation with horseradish peroxidase-conjugated anti-rabbit IgG goat antibody for 1 h at RT. After a final washing, blots were developed in ECL plus reagent (Amersham Biosciences, Piscataway, N.J.).

Transfection. $1\times10^6$ JNCL lymphoblasts were plated in 6-well plates the day of transfection and transfected with pGEM-CLN3 and empty vector control using Lipofectamine™2000 (Invitrogen; Carlsbad, Calif.,) according to the manufacturer's protocol for non-adherent cells. Cells were harvested 48 hours later, homogenized, and subjected to subcellular fractionation as outlined above.

TLC analysis/lipid mass measurements. Lipids were extracted by the Bligh and Dyer method from 250 µl from each subcellular fraction. After methanolysis and measurement of phosphate and protein content, the samples were spotted on borate impregnated TLC-plates (to separate Gal-Cer and GlcCer) and lipids separated using the following solvent system: chloroform/methanol/$NH_4OH$ 2.5 M (65:35:8). A mixture of standards (Qualmix) (Matreya, LLC, Pleasant Gap, Pa.) was used. Total sphingolipids were visualized with primuline and scanned on a Typhoon-101 scanner. Quantification analysis was accomplished with the ImageQuant program. Lipids were normalized to protein content.

Gal-labeling. Normal human and CLN3-deficient lymphoblasts were labeled with $^{14}C$-galactose (Amersham; Piscataway, N.J.) for 3 days in glucose-free RPMI 1640. Cells were harvested, and subcellular fractionation performed. Protein determination for the individual fractions was carried out, followed by lipid extraction with carriers, base hydrolysis, acid neutralization and lipid re-extraction. The dried samples were re-suspended and spotted on to a TLC plate. Glycosphingolipids were scraped after a 2 day film exposure. Results are expressed in counts/minute/microgram (cpm/µg) of protein.

Western Blot. Monoclonal antibodies to flotillin-1, GRASP65 and calreticulin were used to localize the corresponding order and confirm the identity of lipid rafts, Golgi and ER fractions. Fifteen µl was taken from fractions 1-5 and 5 µl was taken from fractions 6-10, mixed with SDS-PAGE sample buffer, boiled and loaded on a 12% polyacrylamide gel for analysis.

RNAi Knockdown of GCT in normal human lymphoblasts. siRNAs were prepared by Stratagene based on the CLN3 gene sequence. siRNA transfection to knock down galactosylceramide synthase (GCT) was achieved using Lipofectamine (Invitrogen) according to manufacturer instructions. For the control, transfection with scrambled siRNA was carried out.

Electron microscopy. Lipid raft fractions obtained following ultracentrifugation using iodixanol (OptiPrep; Norton, Mass.) were suspended with washing buffer (25 mM HEPES, pH 7.4, 150 mM NaCl) and pelleted by ultracentrifugation (20,000 rpm, 30 min, 0° C.). The pellet was fixed with 4% glutaraldehyde, post-fixed for 1 hr in 1% osmium tetroxide ($OsO_4$) in the same buffer, washed in veronal acetate buffer, stained in uranyl acetate in the same buffer, dehydrated in a graded ethanol series and embedded in Poly/Bed 812 (Polysciences, Warrington, Pa.). Thick and thin sections were prepared on a Reichert-Jung ultramicrotome (Leica, Bannockburn, Ill.). Thick sections (0.5 mm) were stained with 1% toluidine blue-borax; thin sections are mounted on copper grids and double-stained with uranyl acetate and lead citrate. Grids were examined using a Philips EM410, 400, or CM 12 electron microscope (FEI; Hillsboro, Oreg.).

Subcellular localization of GalCer. Normal and JNCL cells were double-labeled with antibodies for GalCer and one of a number of specific organellar proteins and subsequently visualized by laser confocal microscopy GalCer, like CLN3, is present in Golgi, lipid rafts, /Rab4- and Rab11-positive endosomes and absent from lysosomes in normal cells. GalCer is markedly diminished in the plasma membrane (PM) and from Rab4-/Rab11-endosomes in JNCL cells. GalCer co-localizes with the Golgi-specific marker, Golgi reassembly structural protein (GRASP65) in both wild-type and JNCL cells. The Golgi complex, however, is fragmented in CLN3 deficient cells. Fragmentation or disruption of the Golgi complex is a hallmark of apoptotic cells and is observed in neurons from a number of neurodegenerative diseases such as Alzheimer's disease, amyotrophic lateral sclerosis and Creutzfeldt-Jakob disease (37-39). GalCer co-localizes with alkaline phosphatase, a lipid raft marker, in normal cells, but not in JNCL cells. The presence of GalCer in Rab4-/Rab11-positive recycling endosomes is confirmed by co-localization with Rab4- and Rab11-markers in normal cells and to a lesser extent in JNCL cells.

These data suggest that GalCer travels the same route as does CLN3p. Similarly to wild type CLN3p, GalCer is largely absent from lysosomes in normal human fibroblasts. In JNCL cells, however, both mutant CLN3p and GalCer localize to lysosomes. This is confirmed by lack of co-localization of GalCer with Cathepsin D, a lysosomal-specific marker in normal cells. The presence and co-localization of CLN3p and GalCer in the same subcellular compartments in normal cells further supports the indication that CLN3p and GalCer trafficking are linked.

Binding of CLN3 to GalCer and sulfatide. Membranes impregnated with sphingolipids were overlaid with protein cell lysates from CLN3-overexpressing and JNCL cells. Anti-CLN3 antibody was used to evaluate binding. Wild-type CLN3p was shown to bind strongly to membrane spots impregnated with sulfatide or GalCer but mutant CLN3 failed to do so. The signal for GalCer-wild-type CLN3p binding was weaker because the more polar sulfatide competes with the less polar GalCer for binding to wild-type CLN3p. When sulfatide was omitted from the membrane, stronger binding of CLN3p to GalCer was observed and this occurred in a dose dependent manner.

GalCer retention in CLN3-deficient ER/Golgi. The rate of synthesis and subcellular distribution of de-novo GalCer and other glycosphingolipids was determined by ($^{14}C$)-galactose labeling of cells, and subcellular fractionation followed by lipid extraction, and TLC analysis (FIG. 1). The levels of de novo GalCer formed are less in LR of CLN3-deficient lymphoblasts as compared to normal. These data indicate that newly synthesized GalCer fails to reach lipid rafts of CLN3-deficient cells, verifying a trafficking defect. Glycosphingolipids, other than GalCer, notably lactosylceramide and globoside are elevated in CLN3-deficient rafts. This may be a compensatory mechanism to overcome low GalCer levels in order to insure raft stability.

Figure 2:
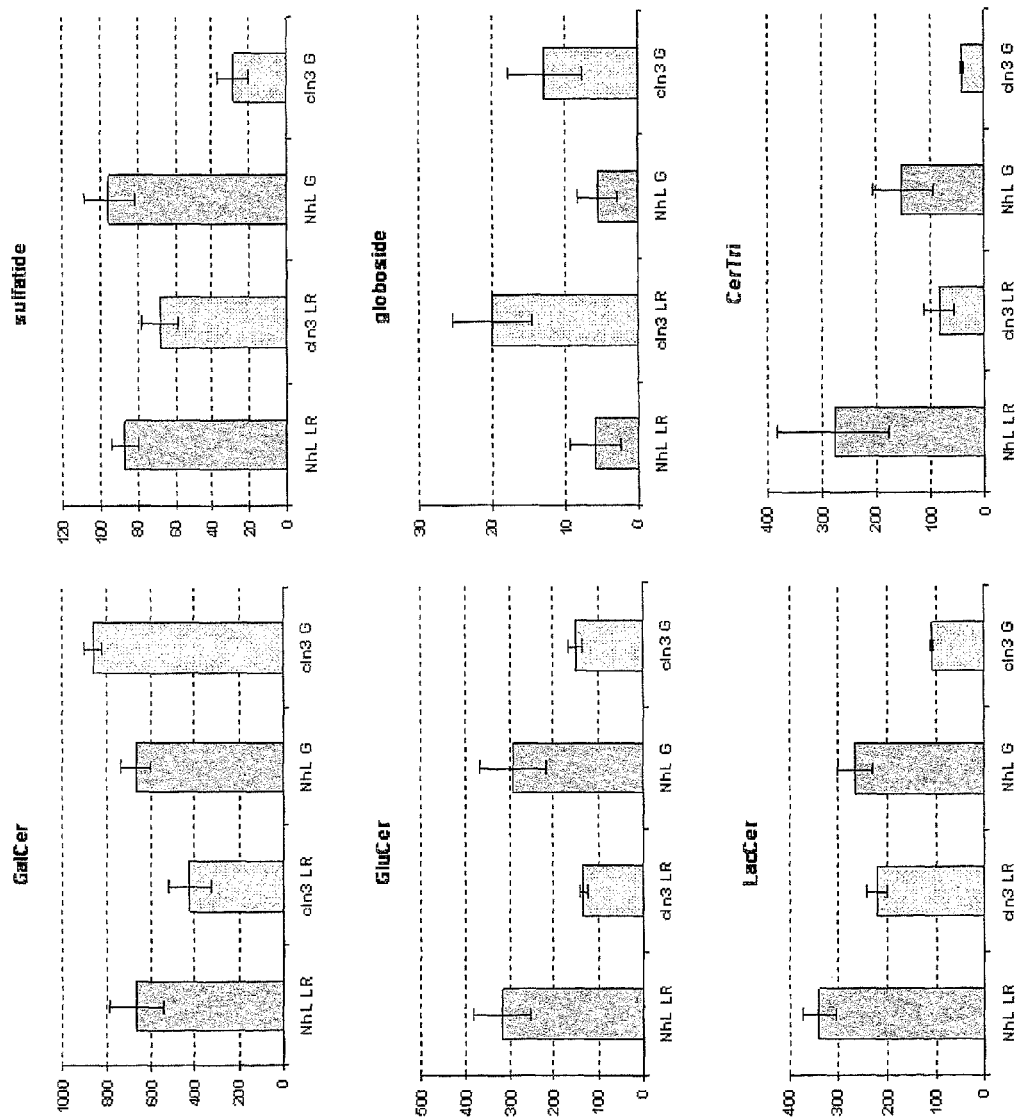
FIG. 2. Mass measurement of glycosphingolipids in JNCL cells. NhL: normal human lymphoblasts; CLN3-deficient: JNCL cells. LR: lipid rafts; G: Golgi; GalCer: galactosylceramide; GlcCer: glycosylceramide; CerTri: ceramide trihexoside. Raft total lipid composition differs between normal and CLN3-deficient cells. Total GalCer raft/Golgi ratio reverses in CLN3-deficient cells compared to normal cells. GlcCer, LacCer and CerTri levels are lower in JNCL cells; globoside is elevated in lipid raft and Golgi fractions; sulfatide is lower in lipid raft fraction from these cells. Total sphingolipids were resolved by TLC, visualized with primuline and scanned on a Typhoon-101 scanner. Quantification analysis was accomplished with the ImageQuant program. Lipids were normalized to protein content. Results are an average of three consecutive experiments; error bars represent the standard error of the mean.

For mass measurement of glycosphingolipids, lipids were collected from subcellular fractions, corresponding to LR, Golgi and ER. Identity of specific subcellular fractions was confirmed by co-localization with the following organelle-specific markers: calreticulin for ER, GRASP65 for Golgi, and flotillin-1 for LRs. Sphingolipid composition of LRs Golgi and ER is altered in JNCL cells (FIG. 2): GalCer is diminished in LRs, but accumulates in Golgi and ER fractions. This corroborates the data of co-localization and retention of CLN3p and GalCer in the ER/Golgi and agrees with de-novo GalCer deposition in CLN3-deficient cells.

Figure 3A:
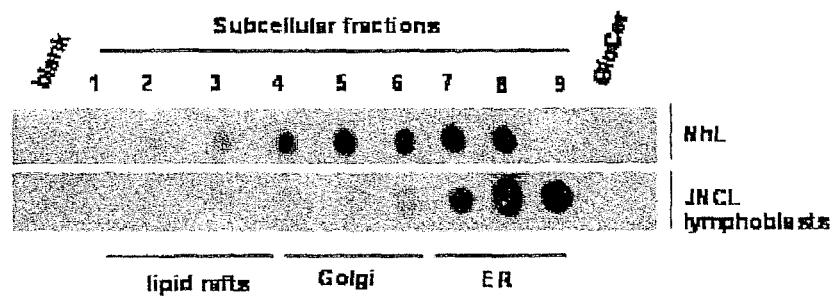
FIGS. 3A-C. JNCL lymphoblast LR fractions are depleted of GalCer. NhL: normal human lymphoblasts; JNCL: Juvenile Neuronal Ceroid Lipofuscinosis; ER: endoplasmic reticulum; GlcCer: glycosylceramide. LR fractions 2-3 are enriched in flotillin-1. Equal amounts of each fraction were applied to the nitrocellulose membrane and probed with anti-GalCer antibody. A. GalCer is abundant in ER and barely detectable in LR fractions compared to normal controls and is barely detectable in lipid raft fractions from JNCL cells. Reintroduction of CLN3p restores GalCer to lipid rafts. B. Western blot (flotillin antibody): maximum flotillin coincides with LR fractions. C. Knockdown of GCT with siRNA leads to reduced GalCer and decreased cell growth. Equal numbers of lymphoblasts (treated with galactosylceramide transferase (GCT) siRNA vs. control siRNA), were counted at 24 (1 day), 48 (2 days), 72 (3 days), 96 (4 days), 120 5 days), 144 (6 days), and 168 hours (7 days).
Figure 3B:
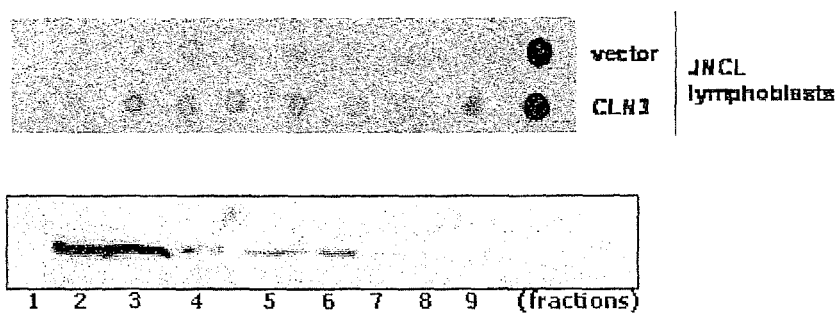

GalCer distribution in subcellular fractions. Subcellular fractions 2 and 3 were shown to have the highest flotillin-1 expression and were designated as LR fractions. Fractions 4, 5, 6, 7 and 8 were positive for GRASP65, corresponding to Golgi fractions. There was some overlap between ER and Golgi fractions 7 and 8 as fractions 7, 8 and 9 were also positive for the ER protein marker, calreticulin. GalCer was evenly distributed in ER (fractions 7 and 8), and Golgi (fractions 4-8), and reached LR (fractions ⅔) in normal cells. A substantial amount of GalCer was retained in the ER and Golgi apparatus of JNCL cells. GalCer was barely present in fraction 3 of LRs derived from JNCL cells (FIG. 3A). Transfection of JNCL cells with a CLN3-containing vector results in the reappearance of GalCer in fraction 3, as opposed to transfection with empty vector (FIG. 3B). The antibody to GalCer is specific for GalCer with no cross-reactivity observed between this antibody and glucosylceramide and sulfatide.

Figure 3C:
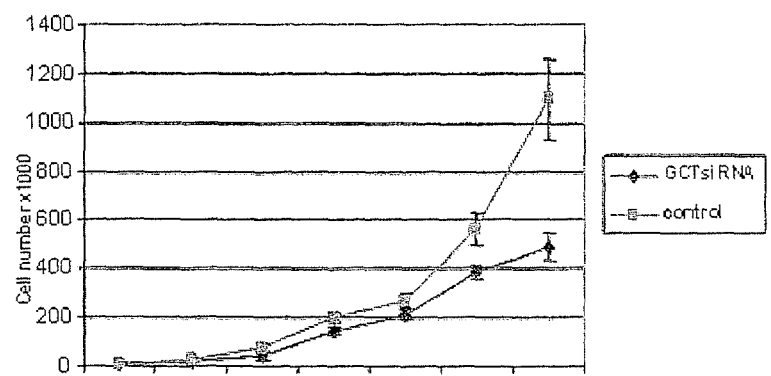

Absence of GalCer. Galactosylceramide transferase (GCT) was successfully knocked down by siRNA in normal cells as verified by quantitative RT-PCR. GalCer visualization by confocal microscopy using a fluorescently labeled GalCer antibody indicated diminished presence of GalCer at the plasma membrane. GCT siRNA transfected cells vs. cells transfected with scrambled siRNA, exhibit diminished growth (FIG. 3C). These results indicate that reducing total cell GalCer diminished GalCer at the plasma membrane and that low GalCer negatively impacts cell growth.

Figure 4:
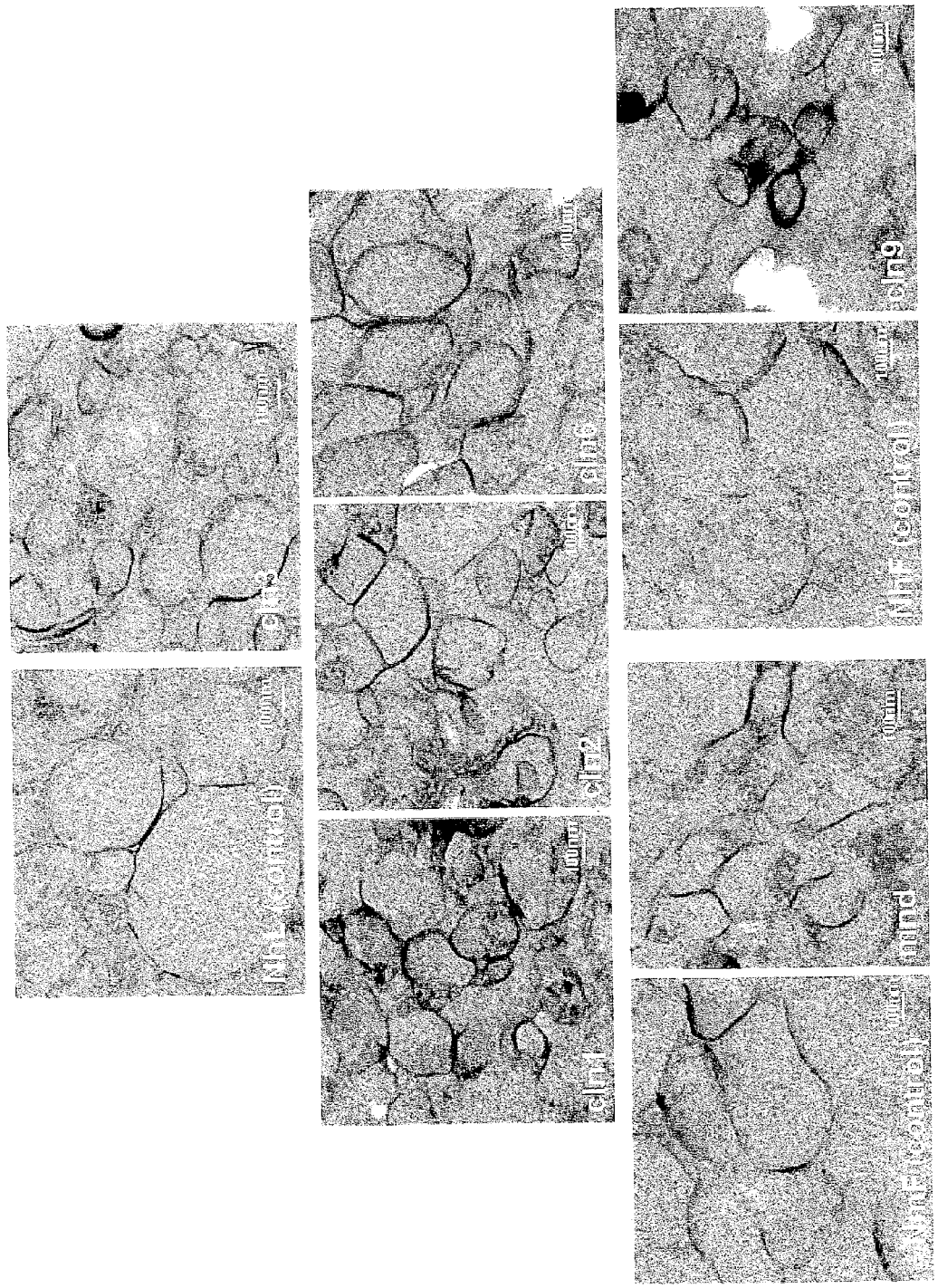
FIG. 4. Electron microscopy of lipid rafts isolated from JNCL or CLN3-deficient, CLN1-, CLN2-, CLN6- CLN8- and CLN9-deficient cells. NhL: normal human lymphoblasts; cln3: CLN3-deficient lymphoblasts; cln1: CLN1-deficient lymphoblasts; cln2: CLN2-deficient lymphoblasts; cln6: CLN6-deficient lymphoblasts; NmF: normal mouse fibroblasts; mnd: CLN8-deficient fibroblasts; NhF: normal human fibroblasts; cln9: CLN9 deficient fibroblasts. Lipid raft subcellular fraction vesicular structures were visualized by electron microscopy (Magnification: 45,000×).

Morphology of lipid rafts in NCL cells. A defined lipid stoichiometry is necessary for physical integrity and structure of rafts. Since sphingolipid profiles of JNCL lipid rafts differ from normal, a change in raft morphology was anticipated. Raft fraction pellets were examined by transmission electron microscopy (TEM). The morphology of the vesicular structures within rafts derived from JNCL cells differed from rafts derived from normal cells. The rafts were smaller in size [50-200 nanometers (nm) in JNCL cells as compared to 300-600 nm in normal cells] and more angular in shape. Likewise, vesicular structures of rafts from CLN1-, CLN2-, CLN6-, CLN8-, and CLN9-deficient cells are angular and smaller in size than those from normal cells (FIG. 4).

Figure 5:
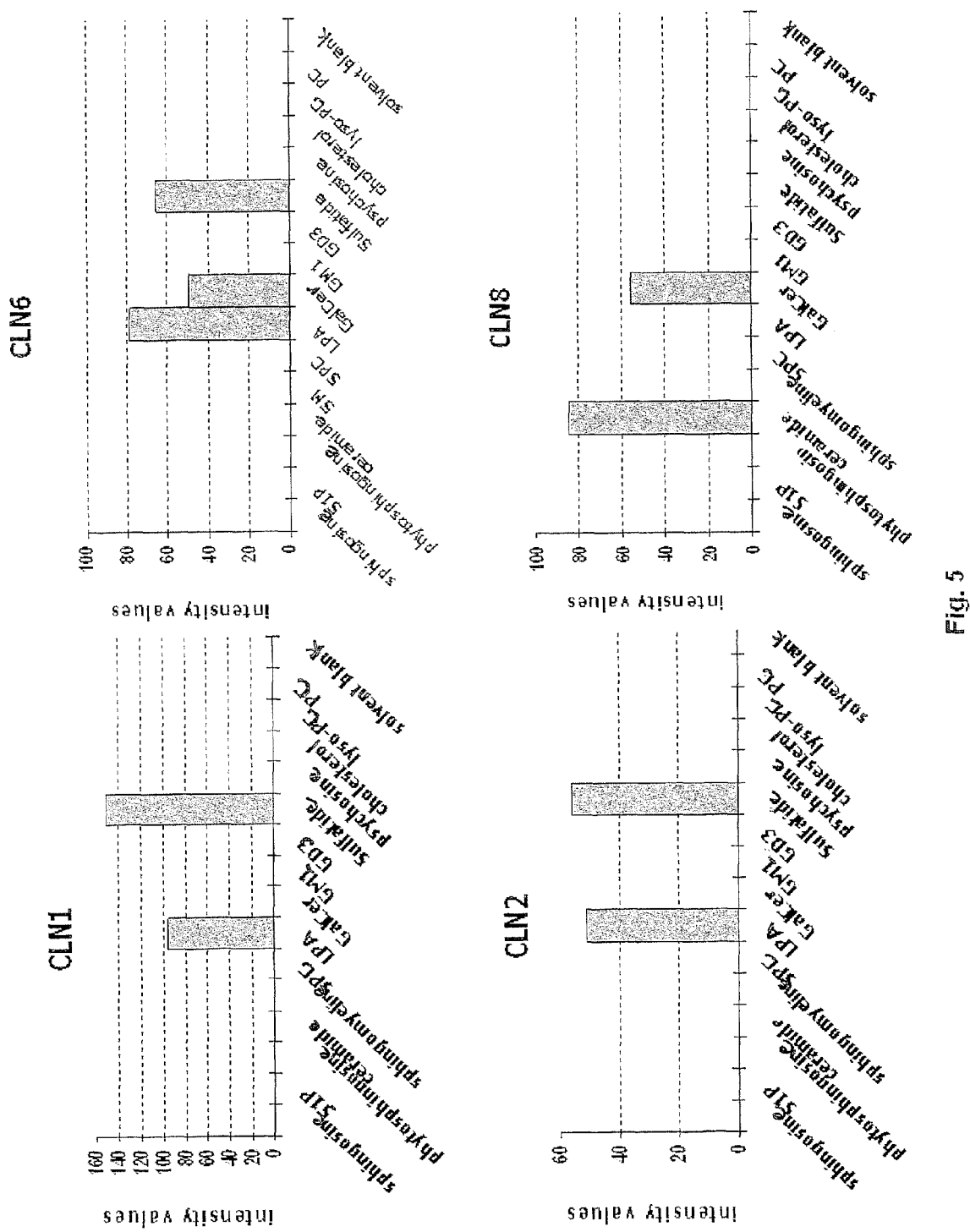
FIG. 5. Lipid binding to CLN1, CLN2, CLN6 and CLN8 proteins using the lipid-protein overlay method. The specific lipids are indicated on the x-axis, and the intensity values for the relative degree of binding of specific lipids to the different NCL proteins are indicated on the y-axis. This experiment was reproduced twice.

CLN1, CLN2, CLN6, CLN8 and CLN9 proteins also bind to lipids. The protein-lipid overlay assay, using custom made sphingostrips, lysates from normal cells and anti-CLN1, anti-CLN2-, anti-CLN6, and anti-CLN8-antibodies, established that CLN6 and CLN8 proteins bind to GalCer, CLN1, CLN2 and CLN6p bind lysophosphatidic acid (LPA) and sulfatide, and CLN8p binds ceramide (FIG. 5).

Figure 6:
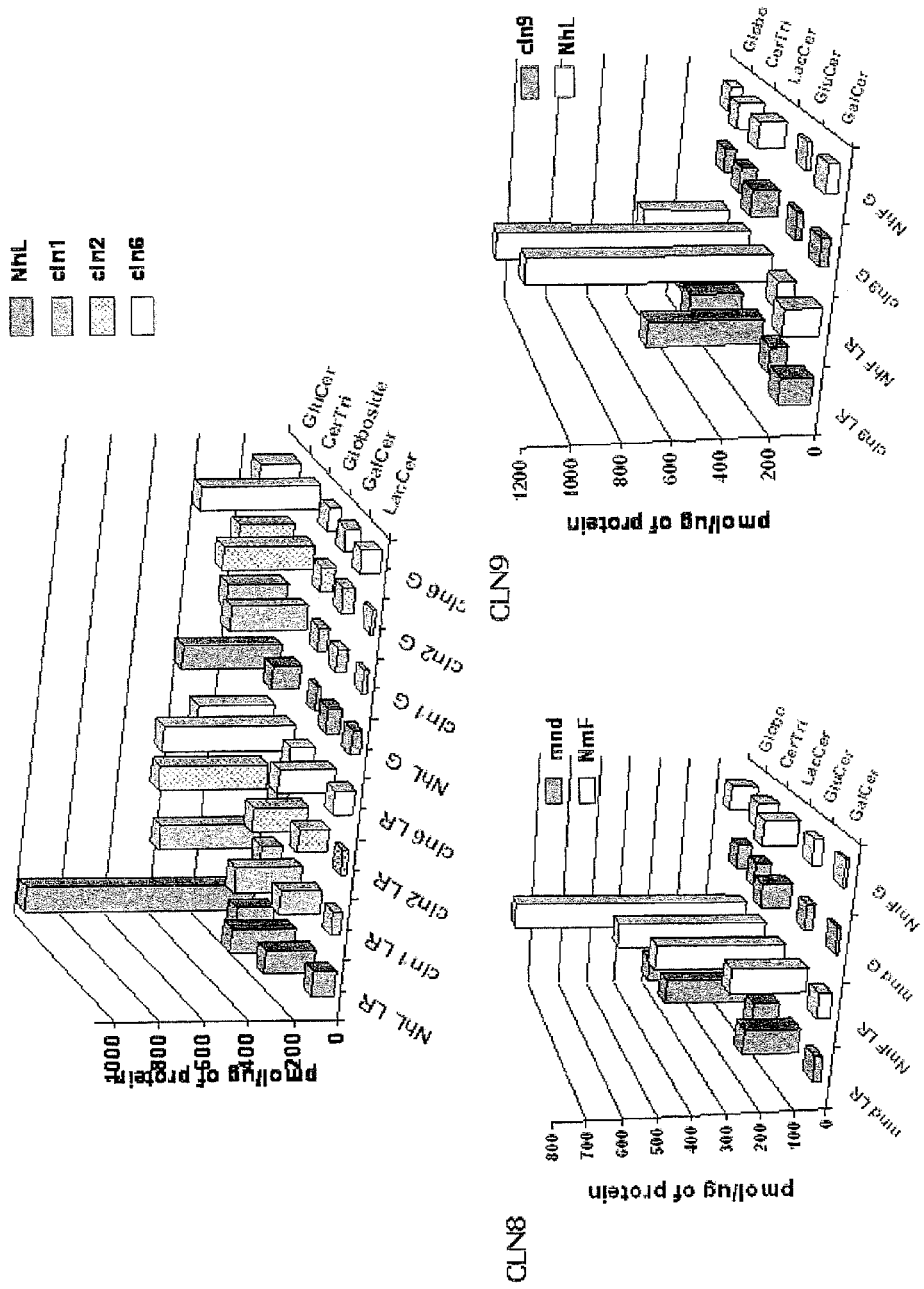
FIG. 6. Raft sphingolipid composition of CLN1-, CLN2-, CLN6-deficient lymphoblasts and CLN8- and CLN9-deficient fibroblasts. Total sphingolipids were extracted from subcellular fractions of normal and NCL diseased human lymphoblasts, resolved by TLC, then scanned on a Typhoon-101 scanner. Quantification was achieved by the ImageQuant program with lipids normalized to protein content. Results were reproduced in three consecutive experiments.

Sphingolipid mass measurement of subcellular fractions from CLN1-, CLN2-, CLN6-, CLN8-, and CLN9-deficient cells. The lipid composition of subcellular fractions corresponding to the Golgi complex and lipid rafts of CLN1-, CLN2-, CLN6-, CLN8- and CLN9-deficient cells was determined. Levels of GalCer, glucoslyceramide (GlcCer), lactosylceramide (LacCer) and ceramide trihexoside and globoside are altered in the different NCL cell lines compared to controls (FIG. 6).

Propidium iodide (PI) staining. Lymphoblasts (treated with GCT siRNA vs. control siRNA) were treated vs. not treated with etoposide and stained with propidium iodide (PI). The percentage of PI positive cells was counted in each. Knockdown of galactosylceramide transferase with siRNA leads to increased apoptosis in CLN3-deficient lymphoblasts, as confirmed by propidium iodide staining. Etoposide augmented the effect of reduced GalCer on apoptosis.

Treatment of CLN3-deficient (JNCL) cells with GalCer increases growth rates. 0.1 million CLN3−/− cells were plated per well in 6 well plates. harvested and counted at 24, 48, 72 and 96 hours. Numbers of viable cells were determined with Trypan blue dye exclusion. Cells were treated with vehicle or GalCer (no treatment or 50 ng/ml or 100 ng/ml. Supplementing JNCL cells with GalCer at a concentration of 50 ng/ml. restored growth. Doubling the concentration of GalCer to 100 ng/ml had no effect.

These studies demonstrate that CLN3 protein is critical for GalCer transport and are the first to link NCL or a Batten protein to the transport of a specific sphingolipid.

Example 2

Animal clinical studies. Studies will be carried out in vivo, to determine if modulation of GalCer levels modifies phenotypes observed in homozygous Cln3$^{\Delta ex7/8}$ mice.

Crossing CLN3 knock-in mice with Twitcher mice. The CLN3$^{\Delta 7/8}$ knock-in mouse model mimics the common genetic mutation in JNCL, making it the ideal model for therapeutic testing in JNCL. The Twitcher mouse, a model of Krabbe disease, is a spontaneous mutant that harbors a genetic defect in the galactosylceramidase (Galc$^{twi}$) gene leading to loss of enzymatic activity and altered catabolism of GalCer. Genetic crosses of the two models will allow a determination of whether increasing GalCer in homozygous Cln3$^{\Delta ex7/8}$ mice will protract JNCL disease course. Compound heterozygote crosses will result in double homozygous mutants (CLN3$^{\Delta ex7/8/\Delta ex7/8}$,Galc$^{twi/twi}$) and single homozygous mutants with one copy of the Twitcher mutant allele, to determine if a single copy modifies the phenotype (CLN3$^{\Delta ex7/8/\Delta ex7/8}$,Galc$^{+/twi}$), Single homozygous mutants and wild-type littermates will be the controls (CLN3$^{\Delta ex7/8/\Delta ex7/8}$,Galc$^{+/+}$; Cln3$^{+/+}$,Galc$^{twi/twi}$ and CLN3$^{+/+}$; Galc$^{+/+}$).

Disease progression will be tested in the following manner. 1) Mice will be weighed daily, beginning at postnatal day 0 (P0). 2) Mice will be observed daily to determine the general state of healthiness. Homozygous Galc$^{twi}$ mice have an average lifespan of ~3 months (Duchen et al., 1980), while homozygous Cln3$^{\Delta ex7/8}$ mice also have reduced survival, but with a later onset, with ~20% of mice dying by 12 months of age. 3) A clasping assay (a 1-minute tail hang assay) and gait analysis will be conducted every other week to assess hindlimb ataxia. 4) A cohort of mice will be pathologically assessed at P0, P7 and 1 month. Mice from the behavioral analyses will also be assessed pathologically when any mouse is deemed moribund or when the experiment ends (at 12 months). In addition to observation of general morphology of the brain, retina and peripheral organs, pathological disease markers will also be measured, including GalCer levels and localization, the JNCL hallmark autofluorescence and subunit c accumulation, gliosis and astrocytosis. Retinal photoreceptor and neuronal counts will also be made, according to standard protocols.

Administration of exogenous GalCer to Cln$^{\Delta ex7/8}$ knock-in mice. To determine whether increasing the levels of GalCer rescues JNCL phenotypes in vivo, a study of exogenous administration of GalCer to CLN3$^{\Delta ex7/8}$ mice will be conducted. This complements the genetic study and will further delineate importance of GalCer trafficking in JNCL, since biosynthetic GalCer and exogenous GalCer traffic differently. Exogenous GalCer is administered as alpha-GalCer or beta-GalCer. GalCer is currently being investigated as a cancer therapy and is documented to be safe in humans. Alpha-GalCer (KRN7000, Kirin Brewery Co., Gunma, Japan or other sources) or beta-GalCer will be injected weekly (via tail vein injections and/or intraperitoneal injections), at a dose of 100 ng/100 grams, into 10 homozygous Cln3$^{\Delta ex7/8}$ mice. As controls, 10 additional homozygous Cln3$^{\Delta ex7/8}$ mice and 10 heterozygous CLN3$^{\Delta ex7/8}$ littermates, which are indistinguishable from wild-type mice, will be vehicle-injected on the same schedule.

Histology and immunostaining. For light and fluorescence microscopic analysis, adult mice will be deeply anesthetized by xylazine/ketamine and sacrificed by cardiac perfusion of ice-cold phosphate-buffered saline (PBS, PH 7.4), followed by periodate-lysine-phosphate (PLP) fixative (2% paraformaldehyde, 0.01M sodium periodate and 0.1M lysine phosphate buffer, pH 7.4). Tissues will be dissected, and fixation continued overnight in PLP fixative at 4° C. Tissues will be collected at 1 week, 3, 6, 10 and 18 months and/or at death and fixed in PLP overnight at 4° C. All tissues will be rinsed, processed, paraffin-embedded and sectioned at 7 mm thickness. For autofluorescence: paraffin sections will be dewaxed in xylene, rehydrated through an ethanol series (2×100%, 2×95%, 2×75%, 50%, 30%), and rinsed in dH$_2$O, Sections will be coverslipped in Vectashield mounting medium (Vector Laboratories) to prevent photobleaching. Autofluorescence will be analyzed at 568 nm on a BioRad Radiance 2100 confocal system (Biorad). Immunostaining will be as follows. Paraffin sections will be dewaxed, rehydrated, and washed in Tris buffered saline (TBS, pH 7.5). Antigen retrieval will be performed (*Human Molecular Genetics* (2002) 11(22):2719) by boiling in citric acid buffer, pH6 (2× boil 5 min, cool 20 min), then incubating in 1% sodium dodecyl sulfate (SDS) at ambient temperature for 5 min. Sections will be rinsed in TBS for removal of SDS and processed for immunostaining using Vectastain ABC-peroxidase staining kits (Vector Laboratories). Antibodies/dilutions are: antisubunit c, 1:500. Biotinylated peanut agglutinin (PNA, 5 mg/ml, Vector Laboratories) will be used to label cone photoreceptors. TUNEL staining will be carried in dewaxed/rehydrated paraffin sections.

Retinal cell counts Peanut agglutinin-stained retinal cross-sections will be viewed under a 20× objective on a light microscope for cell count determination. For each section and 5-6 fields will be counted. Values will be given as average cells per field+/−standard deviation, Only white eyes will be considered in the cell counts. Statistical significance will be determined by a two-tailed Student's t-test.

Behavioral analyses. Mice will be tested for clasping behavior in a 1 min tail-hang assay and scored positive for clasping if limbs are clenched towards the belly for >5 seconds. Three trials, on separate days, will be performed, being blinded to genotype. Gait traces are by walks in a paper-lined tunnel apparatus, of mice with differentially painted hind- and forepaws. Four trials on 2 separate days will be performed for each mouse, and measurements determined by blinded investigators. Statistical significance will be tested in a two-tailed Student's t-test.

Serum collection. Mice will be deeply anesthetized by isofluorane and sacrificed by decapitation, and blood collected and serum separated using Microtainer serum separator tubes (Becton Dickinson). To assess liver function, serum levels of aspartate transaminase (AST) and alanine transaminase (ALT) will be measured with the ALT/AST manual assay kit (Sigma Diagnostics). Alpha-GalCer (KRN7000, Kirin Brewery Co., Gunma, Japan) or beta GalCer will be injected weekly (tail vein injections and/or intraperitoneal injections), at a dose of 100 ng/100 grams, into 10 homozygous Cln3$^{\Delta ex7/8}$ mice. As controls, 10 additional homozygous Cln3$^{\Delta ex7/8}$ mice and 10 heterozygous CLN3$^{\Delta ex7/8}$ littermates, which are indistinguishable from wild-type mice (Cotman et al., 2002), will be vehicle injected on the same schedule. Moreover, since alpha-GalCer is a powerful immunomodulator and JNCL has an autoimmune component (Pearce et al., 2004), which homozygous CLN3$^{3\Delta ex7/8}$ mice replicate, autoantibody status will also be followed by immunoblot assay in the GalCer supplemented mice and the double homozygotes (CLN3$^{\Delta ex7/8/\Delta ex7/8}$,Galc$^{twi/twi}$) from the crosses.

Example 3

Treatment of human subjects. As one example of the embodiments of this invention, a human subject diagnosed with, suspected of having, or at risk of developing, a disorder caused by or associated with a deficiency in a gene product of a CLN gene can be treated according to the methods described herein. For example, to treat JNCL, a human subject can be administered an amount of GalCer intravenously (and/or intrathecally) to achieve a serum concentration of about 10 ng/ml to about 100 ng/ml, as would be readily determined by one of ordinary skill in the art (see, e.g., refs 63-68). The GalCer could be administered weekly or biweekly as needed, including throughout the lifetime of the subject. Clinical parameters that would be monitored to evaluate efficacy include use of a clinical scale with assessment of rate of decline (e.g., the rate of decline would be slower in a treated subject or group of subjects as compared to a nontreated (control) subject or group of control subjects. A degree of cerebral atrophy could be assessed by morphometric MRI analysis of treated vs. untreated subjects and/or an assessment can be made of the amount of apoptosis in leukocytes derived from treated vs. untreated subjects. Another clinical parameter that could be monitored is the number of seizures in a defined period of time.

Example 4

Galactosylceramide in CLN3 Δex7/8 Knock-in Mouse Brain and CLN3 siRNA NT2 Cells and its Effects on Cellular Growth and Apoptosis Cell Culture and Cell Treatment. NT2 neuronal precursor cells (ATCC cat no. CRL 1973) were grown in DMEM supplemented with 1% sodium pyruvate, L-glutamine and antibiotics and incubated in 37 C and 5% CO2 for 3 days.

siRNA knockdown of CLN3 in NT2 cells. HS1 siRNA (TCACGATTTGACTGCAACTCTG) for CLN3 knockdown was designed using BLOCK-iT RNA™ Designer (Invitrogen). 50 μmol siRNA and scrambled universal negative control siRNA oligonucleotides were transfected into wild type NT2 cells using Lipofectamine RNAiMax™ according to manufacturer's protocol. In brief, 6 μmol HS1 RNAi duplex or scrambled siRNA universal negative control were diluted in 50 μl DMEM medium without serum. Lipofectamine™ RNAiMAX was mixed gently before use, then 1 μl was diluted in 50 μl DMEM medium. The diluted RNAi duplexes were combined with the diluted Lipofectamine RNAiMAX and incubated for 10 minutes at room temperature. The RNAi duplex-Lipofectamine™ RNAiMAX complexes were added to cells for a final RNA concentration of 10 nM. Cells were harvested 96 hours post-transfection.

Real-Time PCR validation of CLN3 knockdown. To calculate the effect of CLN3 knockdown following siRNA transfection, RNA from NT2 cells, transfected either with CLN3 siRNA or with scrambled siRNA, was isolated using Trizol reagent (Invitrogen). Reverse transcription was carried out with SuperScript III First-Strand-Synthesis System (Invitrogen). Real Time-PCR was conducted on 500 ng cDNA using /SYBRGreen 10 Mix (Biorad, U.S.A) in a Biorad I-Cycler. Cyclophilin was taken as internal control. To confirm CLN3 knockdown, change in fold expression compared to scrambled siRNA transfected control cells was calculated.

Verification of CLN3 knockdown with immunocytochemistry: To visualize the effect of CLN3 knockdown at the protein level, NT2 cells grown on coverslips in 12-well plates were transfected either with CLN3 siRNA or with scrambled siRNA and incubated at 37° C. and 5% $CO_2$ for 3 days. Cells were fixed with methanol:acetone solution (1/1 in volume) for 5 min then washed with NET gel buffer containing 50 mM Tris-HCl pH 7.5, 150 mM NaCl, 0.1% Triton X-100, 1 mM EDTA pH 8.0 and 0.25% gelatin. Cells were then incubated in 0.5% Triton X-100 diluted in PBS for 5 min. This solution was removed and washed by washing twice with 50 mM glycine/PBS solution. Cells were incubated twice in NET gel buffer, each time for 5 min. Cells were incubated overnight at RT with rabbit primary antibody to CLN3 protein (1:1000 dilution in 90% NET gel, 10% normal horse serum) and washed twice with NET gel buffer, each time for 5 min. Primary antibody was secondarily labeled for 2 hours at RT by goat anti-rabbit antibody (1:200 dilution), covalently-linked to a fluorophore (FITC). One drop of AntiFade™ was finally added to coverslips on glass slides and fluorescence detected with a laser scanning confocal microscope (Zeiss LSM 410).

Determination of cell proliferation rate in CLN3 knockdown NT2 cells. $4\times10^5$ cells transfected with CLN3 siRNA or scrambled siRNA, and treated or not treated with 50 ng/ml GalCer, were seeded and counted with Trypan blue dye exclusion. Each time point represents triplicate samples.

Determination of cell apoptosis rate in CLN3 knockdown NT2 cells. $10^6$ cells transfected with CLN3 siRNA or scrambled siRNA, either treated with 50 ng/ml of GalCer (Avanti Polar Lipids, inc.) or solvent, are suspended in 100 µl PBS, incubated with 100 µl/0.5 mg/ml PI, washed, placed on slides and viewed using a fluorescence microscope. Cells were harvested 3 days after transfection and treatment with GalCer. Cells in three fields of vision were counted. Percentage of red staining-apoptotic cells/total cells was determined.

Mouse experiments. Six homozygous $Cln3^{\Delta ex7/8}$ adult 60 day old mice and six age and sex-matched control mice were deeply anesthetized by xylazine/ketamine and sacrificed by cardiac perfusion of ice-cold phosphate-buffered saline (PBS, pH 7.4), followed by periodate-lysine-phosphate (PLP) fixative (2% paraformaldehyde, 0.01M sodium periodate and 0.1M lysine phosphate buffer, pH 7.4). Mouse brains were snap-frozen in liquid nitrogen. Three of the frozen brains from each group were used for subcellular fractionation and thin layer chromatography, and frozen sections were obtained for fluorescence immunocytochemistry from the rest. At the age of 60 days and two days prior to sacrifice, three of six control mice were injected with α-GalCer at a dose of 6 micrograms grams or vehicle intraperitoneally. They were deeply anesthetized by xylazine/ketamine and sacrificed by cardiac perfusion of ice-cold phosphate-buffered saline (PBS, pH 7.4), followed by periodate-lysine-phosphate (PLP) fixative (2% paraformaldehyde, 0.01M sodium periodate and 0.1M lysine phosphate buffer, pH 7.4). Tissues were snap-frozen in liquid nitrogen and subjected to subcellular fraction and thin layer chromatography for determination of GalCer mass measurements.

Immunocytochemistry of frozen mouse brain. Cryostat frozen sections were fixed on slides using a mix of methanol and acetone at 1:1 ratio for 5 minutes. The slides were then washed with Net gel buffer for 5 minutes. The Net gel buffer was removed and the slides were washed for 5 minutes with 0.5% Triton X-100 in PBS. Next, the slides were incubated twice in 50 mM glycine in PBS for 10 minutes each. Net gel buffer was then used twice for incubation for 5 minutes each. The slides were then incubated overnight at 4° C. in a moist chamber with primary antibody against galactocerebroside (rabbit primary antibody to galactocerebroside, ab2894, Abcam) in a mix of 90% Net gel buffer and 10% normal goat serum. The next day, slides were washed with Net gel buffer 5 times for 5 minutes each. Incubation with secondary antibody conjugated to FITC (goat primary antibody to rabbit IgG conjugated to FITC, ab6718) was done after the washes for 2 hours at room temperature. Fluorosave (Calbiochem, 345789) was then applied and left to dry for 1 hour. Slides were observed using the laser scanning confocal microscope (Zeiss LSM 410).

Mouse brain subcellular fractionation. Tissues were suspended in 0.5 ml of homogenization medium with protease inhibitor (Sigma Protease Inhibitor Cocktail, P8340) (100 µl for every 2 grams of tissue) and disrupted by Dounce homogenization and repeated passages through a fine syringe needle. The homogenate was centrifuged at 2000 rpm for 10 min and the supernatant was harvested. Solutions of 2%, 5%, 10%, 15%, 20%, 25%, 30% and 35% Optiprep were prepared in solution D and layered in 11.5 ml tubes (Sorvall Ultracrimp tube, 03987) from the least to the most dilute. The samples were applied to the top of the gradient and centrifuged at 30,000 rpm for 4 hours (Sorvall Discovery 100SE). Gradients were collected in 0.5 ml fractions. Reagents used include OptiPrep Density Gradient Medium (Sigma, D1556), homogenization medium (150 mM NaCl, 5 mM dithiothreitol, 5 mM EDTA, 25 mM Tris-HCl, pH 7.4), Triton X-100 and solution D (homogenization medium with 1% Triton X-100).

Mouse kidney subcellular fractionation. 0.8 grams of kidney tissue were suspended in 0.5 ml of homogenization medium with protease inhibitor (Sigma Protease Inhibitor Cocktail, P8340) (100 µl for every 2 grams of tissue) and disrupted by Dounce homogenization and repeated passages through a fine syringe needle. The homogenate was centrifuged at 2000 rpm for 10 min and the supernatant was harvested. Solutions of 2% and 25% (w/v) Optiprep solution were prepared by mixing homogenization medium and working solution 24:1 and 1:1 (v/v), respectively. The tubes were sealed well with parafilm and carefully rotated to a horizontal position. They were then left for 45 minutes. The tubes were returned to a vertical position and the sample applied to the top of the gradient and centrifuged at 55,000 rpm for 2.5 hours. Gradients were collected in 0.5 ml fractions. Reagents used include OptiPrep Density Gradient Medium, homogenization medium (0.25 M sucrose, 1 mM EDTA, 10 mM Hepes-NaOH, pH 7.4), diluent (0.25 M sucrose, 6 mM EDTA, 60 mM Hepes-NaOH, pH 7.4), working solution of 50% (w/v) Optiprep (5 vol. of Optiprep+1 vol. of diluent).

Protein isolation from subcellular fractions. To 0.5 ml of each fraction, 2 ml chloroform:methanol (1/2 volume) were added and the mixture vortexed for 1 min. 0.625 ml chloroform was then added twice and solutions intermittently mixed for 1 min then centrifuged at 1700 rpm for 10 min at 4° C. Supernatants were collected to a new tube, 0.3 ml chloroform added, then mixtures centrifuged at 1900 rpm for 10 seconds. To each mixture, 0.3 ml water were added followed by vigorous mixing then centrifugation at 1900 rpm for 1 min. Upper phase was discarded and to the remaining interphase and lower phase 0.3 ml methanol was added. Following mixing, tubes were centrifuged at 1900 rpm for 2 min to pellet the proteins. The interphase was discarded, and the lower phase kept for lipid extraction. The pellet was dissolved in 50 μl TBS and 15 μl NaOH 1M. Protein concentration was then determined with Biorad DC protein assay according to the manufacturer's protocol.

Lipid extraction from subcellular fractions. For each fraction, 250 μl were taken from the lower phase and subjected to speed vacuum for liquid evaporation. Lipids were dissolved by adding 200 μl chloroform:methanol (2:1).

Phosphate determination. Lipids samples were vacuum dried for 20 minutes. After the drying of the samples, 150 ul of 70% perchloric acid were added to them and to dilutions of disodium hydrogen phosphate ($Na_2HPO_4$) standards. Tubes were capped with glass balls previously soaked in methanol and placed on a hot plate at 180 degrees for 1 hour. Tubes were then left to cool down for 10 minutes at room temperature and 830 μl of distilled water, 170 μl of 2.5% ammonium molybdate and 170 μl of 10% ascorbic acid were added and tubes vortexed each time. Mixtures were incubated for 15 minutes in a waterbath at 50° C., then cooled down for 2 minutes and concentration determined with a spectrophotometer at 820 nm wavelength.

Thin Layer Chromatography for Quantification of Galactosylceramide. After methanolysis and measurement of phosphate and protein concentration, lipid samples from the different subcellular fractions were spotted on borate-impregnated TLC plates and lipids separated using a mixture of chloroform, methanol and $NH_4OH$ 2.5 M (65:35:8) for 2 hours. 20 and 40 μg of galactosylceramide standard and a mixture of standards (Qualmix, Matreya, LLC, Pleasant Gap, Pa.) were used. Plate was air-dried, dipped into PBS solution for 5 minutes and then incubated with 1% primuline solution in the dark. It was then washed with PBS for 10 minutes, dried with a fan and scanned on StormReader™. Lipid quantification was accomplished with ImageQuant™ program and normalized with respect to phosphate content.

Figure 7:
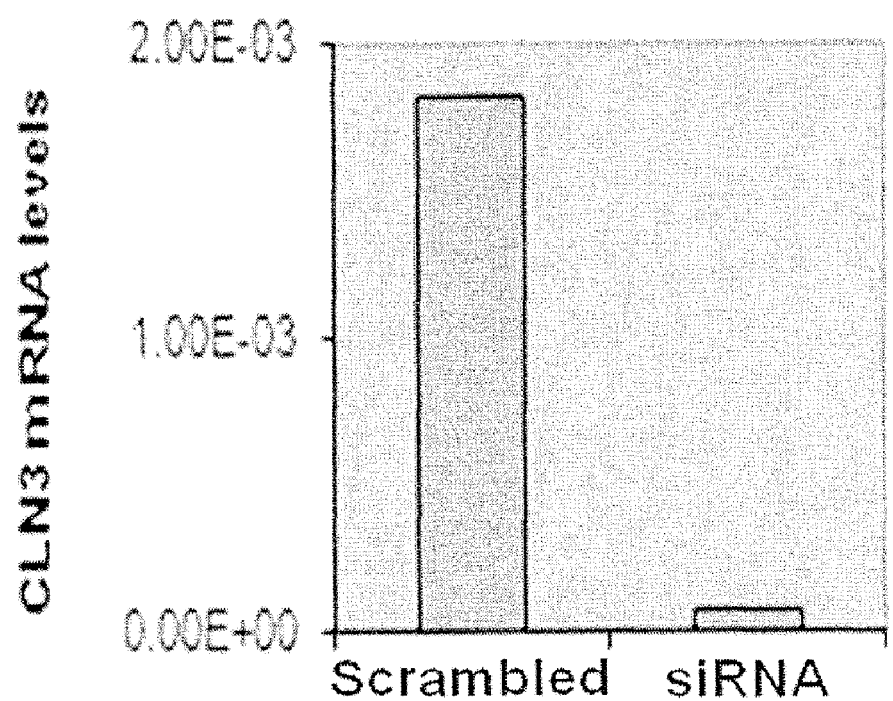
FIG. 7. siRNA-transfected NT2 cells show a 22 fold-decrease in CLN3 expression, compared to WT, 3 days following transfection.

Verification of CLN3 knockdown in NT2 cells. Short interfering RNA (siRNA) specifically targeting CLN3 transcript was designed and used. Real time-PCR was conducted to check the levels of expression of CLN3 in the resulting mutant NT2 cell line. Compared to NT2 cells transfected with scrambled siRNA, siRNA knockdown cells (HS1) displayed a 22-fold decrease in CLN3 expression 3 days post-transfection (FIG. 7).

To further validate CLN3 knockdown at the protein level, immunocytochemistry was performed on NT2 cells transfected either with scrambled or CLN3 siRNA. Compared to NT2 cell line transfected with scrambled siRNA, the HS1 cell line showed very significant reduction in CLN3 expression, denoted by decreased FITC fluorescence intensity.

NT2 cell proliferation and apoptosis rates. An equal number of NT2 cells was initially seeded and cell number determined at different time points with Trypan blue dye exclusion. Each time point represents 2 experiments. Reducing CLN3 expression by siRNA diminished GalCer levels, negatively impacting cell growth.

Figure 8:
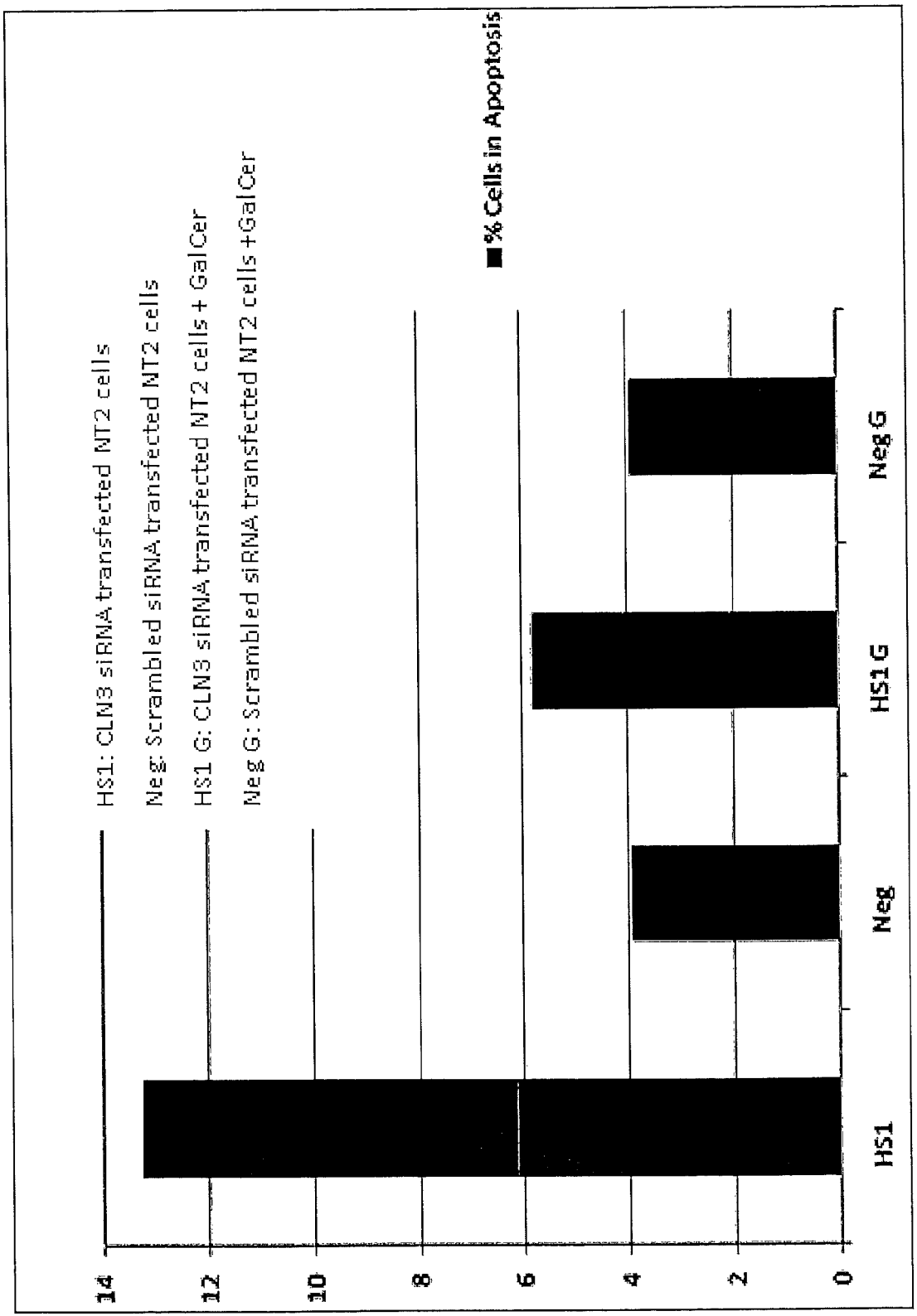
FIG. 8. CLN3 −/− NT2 cells (HS1) displayed a 2.4 fold increase in apoptosis compared to wild type (Neg), 3 days post-transfection. Exogenous supplements of GalCer significantly reduced cell death (HS1 G).
Figure 9:
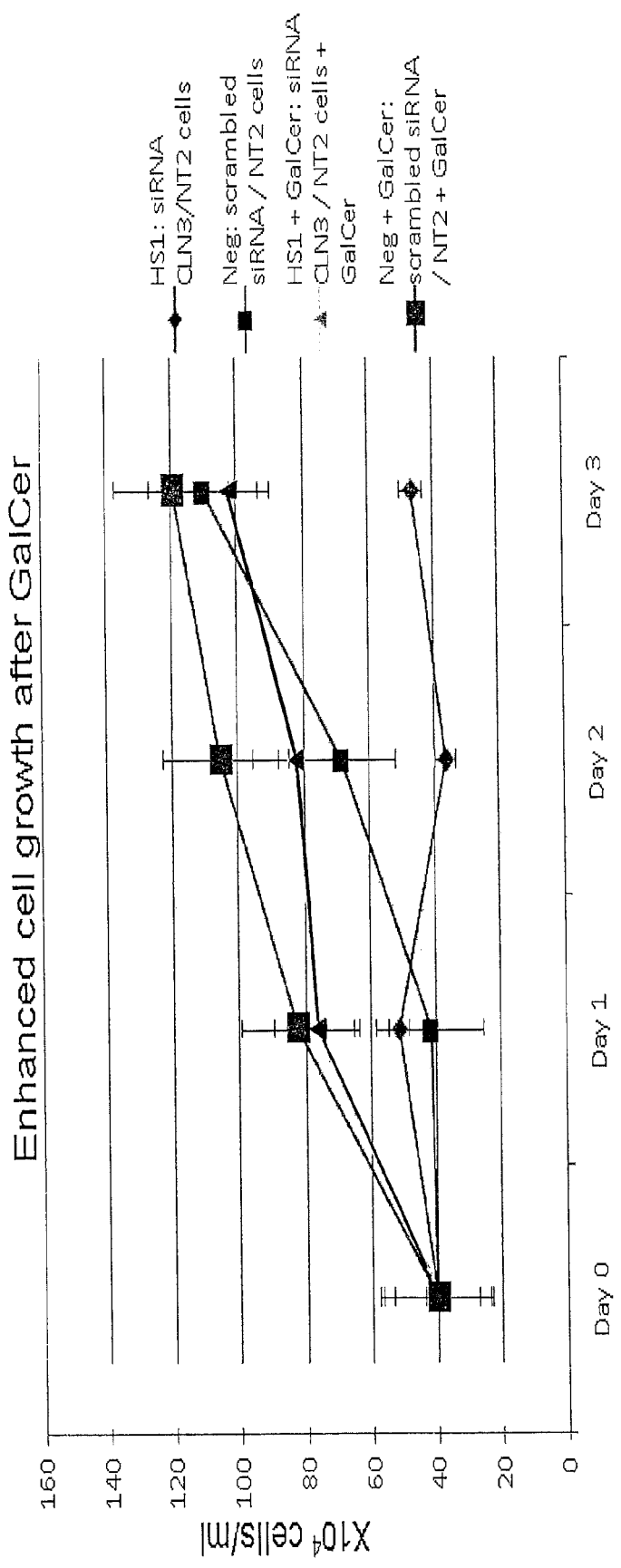
FIG. 9. CLN3 −/− NT2 cells (diamonds) display 58% decrease in growth 3 days post-transfection, compared to WT (squares). Exogenous supplementation of GalCer normalized growth (triangles).

CLN3-deficient NT2 cells displayed a 58% decrease in growth and 2.4 fold increase in apoptosis 3 days post-transfection, in comparison to the WT-NT2 cells (FIGS. 8-9). Cells were treated with vehicle or 50 ng/ml of GalCer. Exogenous GalCer supplementation normalized growth and significantly reduced cell death of the CLN3-deficient NT2 cells.

Figure 10:
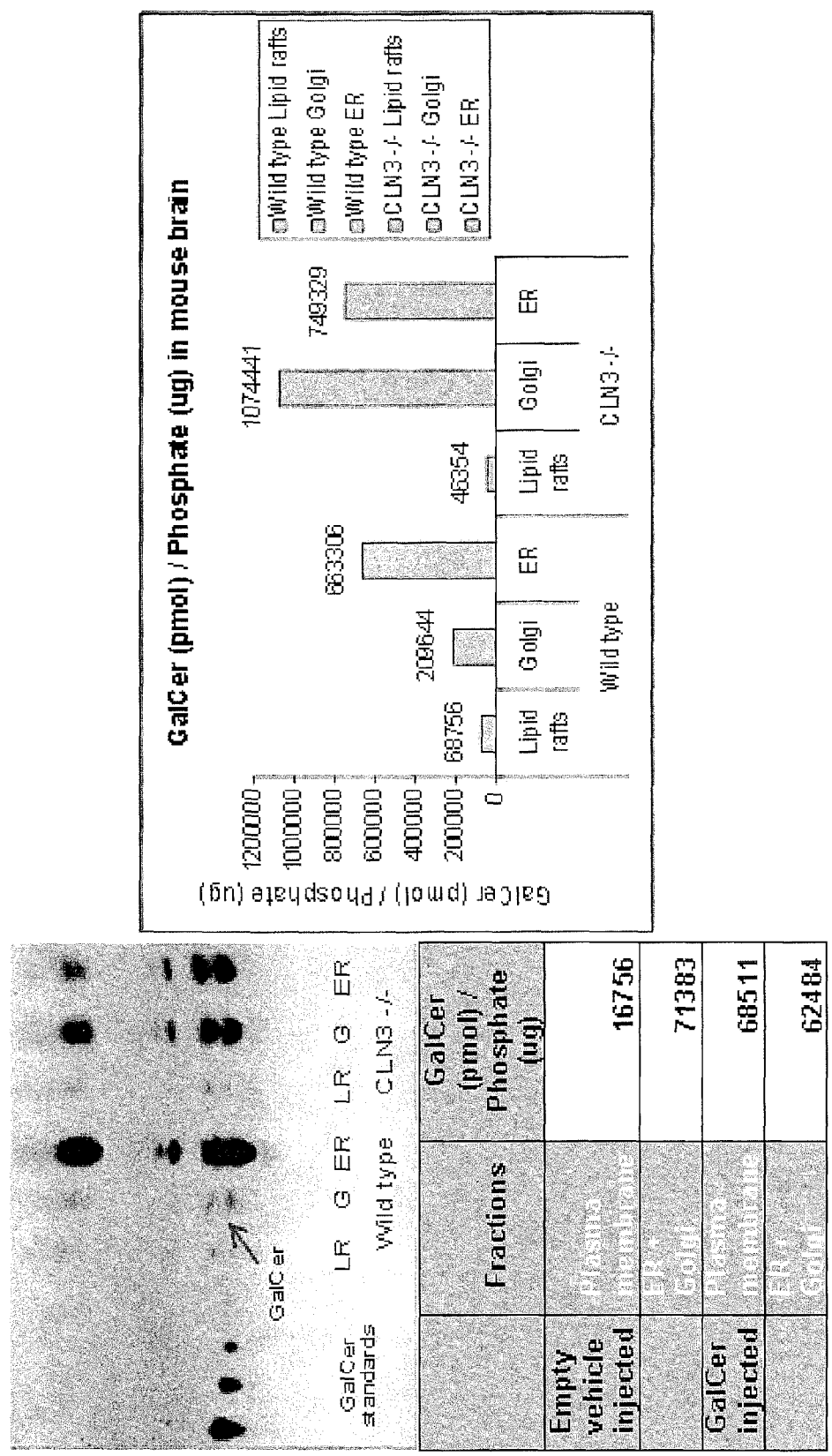
FIG. 10. Thin layer chromatography of lipids obtained from subcellular mouse brain fractions. The image was scanned into a Stormreader and GalCer mass measurements normalized to phosphate and depicted in a bargraph. There is a deficit in lipid raft GalCer and a much greater retention of GalCer in Golgi derived from homozygous CLN3Δex7/8 knock-in mouse brain compared to wild type control FIG. 11. Intraperitoneal GalCer injections of normal mice increases kidney lipid raft GalCer with a concomitant drop in Golgi GalCer.

GalCer in WT and CLN3 Δex718 knock-in mouse brain. WT and CLN3 Δex7/8 knock-in mice brain tissue was subjected to subcellular fractionation. Total proteins were extracted and then total lipids were isolated from the LR, Golgi and ER fractions, and phosphate levels were determined for each fraction. Equal amounts of total lipids, normalized to phosphate levels in each fraction, were separated on a TLC plate and stained with primuline. The TLC plate was scanned using StormReader™ and quantitative analysis was performed with ImageQuant™ software. Compared to WT control, GalCer levels in the fractions (3F) of homozygous CLN3Δex7/8 knock-in mouse brain show approximately a 2-fold increase, in Golgi (Table 1). In CLN3Δex7/8 knock-in mouse brain Golgi, GalCer constitutes 57.45% of 3F-GalCer, while in WT it accounts for 22.82%. In CLN3Δex7/8 knock-in mouse brain ER, GalCer constitutes 40.07% of 3F-GalCer while in WT it accounts for 69.93%. In CLN3Δex7/8 knock-in mouse brain LR, GalCer constitutes 2.48% of 3F-GalCer while in WT it accounts for 7.25% (FIG. 10).

Figure 11:
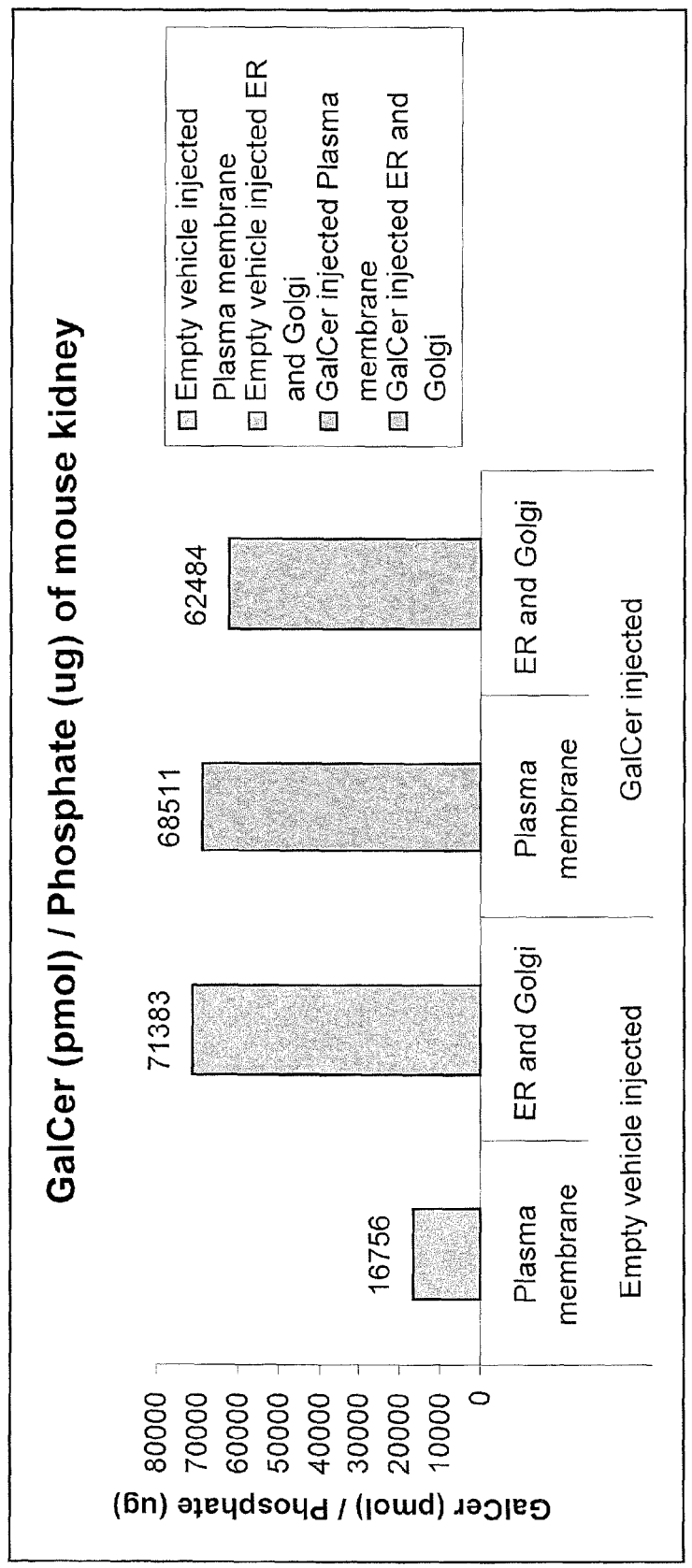

Data presented from mice injected with GalCer intraperitoneally confirms the ability to increase GalCer at the plasma membrane in mouse tissues with a concomitant reduction in Golgi GalCer (FIG. 11). A long-term therapeutic trial in CLN3Δex7/8 knock-in mice injected intraperitoneally with GalCer is underway.

In this study, it was demonstrated that a decrease of GalCer in CLN3-deficient human NT2 neuronal precursor cells may underlie the significant decrease in growth and increase in apoptosis. Exogenous GalCer supplementation normalizes GalCer in lipid rafts, corrects growth and significantly reduces cell death in these cells. GalCer synthase knockdown results in the diminution of GalCer in lymphoblasts with a deleterious effect on cell growth and an increase in apoptosis that are also remedied by exogenous supplementation of GalCer (Rusyn E et al., 2008). GalCer and sulfated GalCer are also found in the retina (Matsui et al., 1987). Rusyn and co-workers (2008) designated CLN3 as a facilitator of GalCer transport from ER/Golgi to LRs in lymphoblasts.

Brain obtained from CLN3Δex7/8 knock-in mice supports this finding with a reduction in lipid raft GalCer and a relative increase in Golgi GalCer. A 2-fold overall GalCer level increase is observed, notably in the Golgi fraction with GalCer retention in the Golgi, with decreased LR and ER GalCer levels in CLN3Δex7/8 knock-in mouse brain (65.8% and 42.7% loss of GalCer content in LR and ER, respectively).

Together, GalCer and its derivative, sulfated GalCer or sulfatide constitute approximately 30% of total myelin lipid, and are first expressed at a critical point during oligodendrocyte differentiation, when progenitors cease to proliferate and commence terminal differentiation (Honke et al., 2002). GalCer is a major component of myelin/oligodendrocyte PM (Hirahara et al., 2004) and of neuronal axons. It is a precursor to sulfated GalCer or sulfatide, which mediates diverse biological processes including the regulation of cell growth, protein trafficking, signal transduction, cell adhesion, neuronal plasticity and morphogenesis (Ishizuka, 1997).

These results indicate that the JNCL cellular phenotype maybe due to failure of GalCer to reach lipid rafts. Correction of the GalCer deficit in neuronal cells results in alleviation of cell growth and apoptotic defects. The mechanism for this is unclear, but presumably re-establishing a correct sphingolipid stoichiometry in lipid rafts at the plasma membrane restores pro-growth signaling functions. LRs isolated from JNCL lymphoblasts are known to exhibit changes in vesicular size and glycosphingolipid content. LRs are important for normal synapse density and morphology in the central nervous system, myelin integrity and myelin-axonal interactions. They harbor ceramide, a proapoptotic lipid second messenger. Ceramide and its precursor dihydroceramide are the building blocks for sphingomyelin, GalCer, sulfatide, glucosylceramide, lactosylceramide, gangliosides and other glycosphingolipids. Also, LRs house caspase-8, the first initiator caspase to activate in the apoptotic cascade in CLN3−/− cells.

A lipid raft GalCer deficit in CLN3Δex7/8 knock-in mouse brain indicates that exogenous GalCer supplementation in these mice may help prevent the neurological deficit observed in these mice, or at least slow-down the neurodegenerative process.

The foregoing is illustrative of the present invention, and is not to be construed as limiting thereof. The invention is defined by the following claims, with equivalents of the claims to be included therein. All publications, patent applications, patents, patent publications, sequences (nucleotide sequences, single polymorphism nucleotides, amino acid sequences, etc.) identified in the GenBank® database or other sequence databases and any other references cited herein are incorporated by reference in their entireties for the teachings relevant to the sentence and/or paragraph in which the reference is presented.

REFERENCES

Alexianu M E, Manole E, Engelhardt J I, Appel S H. 2000; Ultrastructural evidence of calcium involvement in experimental autoimmune gray matter disease. *J Neurosci Res* 60: 98-105.

Biswas S, Heetveld S, Wolf P, Cao Y, Norton S, Haggarty S, Hrabe de Angelis M, Cotman S. 2009; Proc 12th International Congress on Neuronal Ceroid Lipofuscinosis (NCL), Hamburg—Germany.

Cao Y, Espinola J A, Fossale E, Massey A C, Cuervo A M, MacDonald M E, Cotman S L. 2006; Autophagy Is Disrupted in a Knock-in Mouse Model of Juvenile Neuronal Ceroid Lipofuscinosis. *J Biol Chem* 281: 20483-20493.

Chang J W, Choi H, Kim H J, Jo D G, Jeon Y J, Noh J Y, Park W J, Jung Y K. 2007; Neuronal vulnerability of CLN3 deletion to calcium-induced cytotoxicity is mediated by calsenilin, *Hum. Mol. Genet.* 16: 317-326.

Chattopadhyay S, Muzaffar N E, Sherman F, Pearce, D A. 2000; The yeast model for Batten disease: mutations in BTN1, BTN2 and HSP30 alter pH homeostasis. *J. Bacteriol.* 182: 6418-6423.

Codlin S, Haines R L, Mole S E. 2008; btn1 Affects Endocytosis, Polarization of Sterol-Rich Membrane Domains and Polarized Growth in *Schizosaccharomyces pombe*. *Traffic* 9: 936-950.

Cotman S L, Vrbanac V, Lebel L A, Lee R L, Johnson K A, Donahue L R, Teed A M, Antonellis K, Bronson R T, Lerner T J, MacDonald M E. 2002; Cln3 Dex7/8 knock-in mice with the common JNCL mutation exhibit progressive neurologic disease that begins before birth. *Human Molecular Genetics* 11: 2709-2721.

Demestre M, Howard R S, Orrell R W, Pullen A H. 2006; Serine proteases purified from sera of patients with amyotrophic lateral sclerosis (ALS) induce contrasting cytopathology in murine motoneurones to IgG. *Neuropathol Appl Neurobiol* 32: 141-156.

Ezaki J, Takeda-Ezaki M, Koike M, Ohsawa Y, Taka H, Mineki R, Murayama K, Uchiyama Y, Ueno T, Kominami E. 2003; Characterization of Cln3p, the gene product responsible for juvenile neuronal ceroid lipofuscinosis, as a lysosomal integral membrane glycoprotein, *J Neurochem* 87: 1296-1308.

Fantini J, Garmy N, Mahfoud R, Yahi N. 2002; Lipid rafts: structure, function and role in HIV, Alzheimer's and prion diseases. *Expert Rev Mol Med* 202: 1-22.

Fossale E, Wolf P, Espinola J A, Lubicz-Nawrocka T, Teed A M, Gao H, Rigamonti D, Cattaneo E, MacDonald M E, Cotman S L. 2004; Membrane trafficking and mitochondrial abnormalities precede subunit c deposition in a cerebellar cell model of juvenile neuronal ceroid lipofuscinosis. *BMC Neurosci.* 5: 57.

Gachet Y, Codlin S, Hyams J S, Mole S E. 2005; btn1, the *Schizosaccharomyces pombe* homologue of the human Batten disease gene CLN3, regulates vacuole homeostasis. *J Cell Science* 118: 5525-5536.

Golabek A A, Kida E, Walus M, Kaczmarski W, Michalewski M, Wisniewski K E. 2000; CLN3 protein regulates lysosomal pH and alters intracellular processing of Alzheimer's amyloid-beta protein precursor and cathepsin D in human cells, *Mol. Genet. Metab.* 70: 203-213.

Griesbeck O, Baird G S, Campbell R E, Zacharias D A, Tsien R Y. 2001; Reducing the environmental sensitivity of yellow fluorescent protein. Mechanism and applications. *J Biol Chem* 276: 29188-29194.

Gubser C, Bergamaschi D, Hollinshead M, Lu X, van Kuppeveld F J, Smith G L. 2007; A new inhibitor of apoptosis from vaccinia virus and eukaryotes. *PLoS Pathog.* 3: 246-259.

Hobert J A, Dawson G. 2007; A novel role of the Batten disease gene CLN3: association with BMP synthesis. *Biochem. Biophys. Res. Commun.* 358: 111-116.

Holopainen J M, Saarikoski J, Kinnunen P K, Jarvela I. 2001; Elevated lysosomal pH in neuronal ceroid lipofuscinoses (NCLs). *Eur J Biochem:* 268: 5851-5856.

Honke K, Hirahara Y, Dupree J, Suzuki K, Popko B, Fukushima K, Fukushima K, Nagasawa T, Yoshida N, Wada Y, Taniguchi N. 2002; Paranodal junction formation and spermatogenesis require sulfoglycolipids. *Proc Nat Acad Sci* 99: 4227-4232.

Ishizuka I. 1997; Chemistry and functional distribution of sulfoglycolipids. *Prog Lipid Res* 36: 245-319.

Kama R, Robinson M, Gerst J E. 2007; Btn2, a Hook1 ortholog and potential Batten disease-related protein, mediates late endosome-Golgi protein sorting in yeast. *Mol Cell Biol* 27: 605-621.

Kasri N N, Kocks S L, Verbert L, Hebert S S, Callewaert G, Parys J B, Missiaen L, De Smedt H.2006; Up-regulation of inositol 1,4 5-trisphosphate receptor type 1 is responsible for a decreased endoplasmic reticulum Ca2+ content in presenilin double knock-out cells. *Cell Calcium* 40: 41-51.

Kyttala A, Ihrke G, Vesa J, Schell M J, Luzio J P. 2004; Two motifs target Batten disease protein CLN3 to lysosomes in transfected nonneuronal and neuronal cells, *Mol. Biol. Cell* 15: 1313-1323.

Lane S C, Jolly R D, Schmechel D E, Alroy J, Boustany R M. 1996; Apoptosis as the mechanism of neurodegeneration in Batten's disease, *J. Neurochem.* 67: 677-683.

Lin P, Yao Y, Hofineister R, Tsien R Y, Farquhar M G. 1999; Overexpression of CALNUC (nucleobindin) increases agonist and thapsigargin releasable $Ca^{2+}$ storage in the Golgi. *J Cell Biol* 145: 279-289.

Luiro K, Yliannala K, Ahtiainen L, Maunu H, Jarvela I, Kyttala A, Jalanko A. 2004; Interconnections of CLN3, Hook1 and Rab proteins link Batten disease to defects in the endocytic pathway. *Hum. Mol. Genet.* 13: 3017-3027.

Mahfoud R, Garmy N, Maresca M, Yahi N, Puigserver A, Fantini J. 2002; Identification of a common sphingolipid-binding domain in Alzheimer, prion, and HIV-1 proteins. *J Biol Chem* 277: 11292-11296.

Mao Q, Foster B, Xia H, Davidson B L. 2003; Membrane topology of CLN3, the protein underlying Batten disease. *FEBS Lett* 541: 40-46.

Martone M E, Edelmann V M, Ellisman, M H, Nef P. 1999; Cellular and subcellular distribution of the calcium-binding protein NCS-1 in the central nervous system of the rat *Cell Tissue Res* 295: 395-407.

Matsui E, Ogura K, Handa S. 1987; Glycolipids of the bovine pineal organ and retina. *J Biochem* 101:423-432.

Mitchison H M, Bernard D J, Greene N D et al. 1999; Targeted disruption of the Cln3 gene provides a mouse model for Batten disease. *Neurobiol Dis* 6: 321-334.

Mitchison H M, Lim M J, Cooper J D. 2004; Selectivity and types of cell death in the neuronal ceroid lipofuscinoses. *Brain Pathol.* 14: 86-96.

Narayan S B, Rakheja D, Tan L, Pastor J V, Bennett M J. 2006; CLN3P, the Batten's disease protein, is a novel palmitoyl-protein Delta-9 desaturase, *Ann. Neurol.* 60: 570-577.

Pearce D A, Ferea T, Nosel S A, Das B, Sherman F. 1999; Action of BTN1, the yeast orthologue of the gene mutated in Batten disease. *Nat. Genet.* 22: 55-58.

Persaud-Sawin D, McNamara II J O, Rylova S, Van Dongen A, Boustany R M. 2004; A galactosylceramide binding domain is involved in trafficking of CLN3 from Golgi to rafts via recycling endosomes. *Pediatric Research* 56: 449-463.

Pontikis C C, Cella C V, Parihar N, Lim M J, Chakrabarti S, Mitchison H M, Mobley W C, Rezaie P, Pearce D A and Cooper J D. 2004; Late onset neurodegeneration in the Cln3)/) mouse model of juvenile neuronal ceroid lipofuscinosis is preceded by low level glial activation. *Brain Res.* 1023: 231-242.

Ramirez-Montealegre D, Pearce D A. 2005; Defective lysosomal arginine transport in juvenile Batten disease. *Hum. Mol. Genet.* 14: 3759-3773.

Rusyn E, Mousallem T, Miller S, Boustany R M. 2008; CLN3p impacts Galactosylceramide Transport, Raft Morphology and Lipid Content. *Pediatric Research* 63: 625-31.

Sepúlveda M R, Marcos D, Berrocal M, Raeymaekers L, Mata A M, Wuytack F. 2008; Activity and localization of the secretory pathway Ca2+-ATPase isoform 1 (SPCA1) in different areas of the mouse brain during postnatal development. *Mol Cell Neurosci* 38: 461-73.

Simons K, Ikonen E. 1997; Functional rafts in cell membranes. Nature 387: 569-572. Storch S, Pohl S, Quitsch A, Falley K, Braulke T. 2007; C-terminal prenylation of the CLN3 membrane glycoprotein is required for efficient endosomal sorting to lysosomes. Traffic 8: 431-4

Southall T D, Terhzaz S, Cabrero P, Chintapalli V R, Evans J M, Dow J A, Davies S A, 2006; Novel subcellular locations and functions for secretory pathway Ca2+/Mn2+-ATPases. *Physiol Genomics* 26: 35-45.

Sutton J M, Chow-Worn O, Spaven L, Silman N J, Hallis B, Shone C C. 2001 Tyrosine-1290 of tetanus neurotoxin plays a key role in its binding to gangliosides and functional binding to neurones. *FEBS Lett* 493: 45-49.

The International Batten Disease Consortium. 1995; Isolation of a novel gene underlying Batten disease, CLN3. *Cell* 82: 949-957.

Uusi-Rauvaa K, Luiroa K, Tanhuanpääb B, Koprac O, Martin-Vasallod P, Kyttäläa A, Jalanko A. 2008; Novel interactions of CLN3 protein link Batten disease to dysregulation of fodrin—$Na^+$, $K^+$ ATPase complex. *Exp Cell Res* 314: 2895-2905.

Vanoevelen J, Raeymaekers L, Dode L, Parys J B, De Smedt H, Callewaert G, Wuytack F, Missiaen L. 2005; Cytosolic Ca2+ signals depending on the functional state of the Golgi in HeLa cells. *Cell Calcium* 38: 489-495.

von Figura K, Gieselmann V, Jaeken J (2001) Metachromatic leukodystrophy. In: *The metabolic and molecular basis of inherited disease* (Scriver C R, Beaudet A L, Valle D, Sly W S, eds.), pp 3695-3724. New York: McGraw-Hill.

Wisniewski K E, Rapin I, Heaney-Kieras J. 1988; Clinicopathological variability in the childhood neuronal ceroid-lipofuscinoses and new observations on glycoprotein abnormalities. *Am. J. Med Genet*, 5(Suppl): 27-46.

Wuytack F, Raeymaekers L, Missiaen L. 2003; PMR1/SPCA Ca2+ pumps and the role of the Golgi apparatus as a Ca2+ store. *Pflugers Arch.* 446: 148-153.

1. Boustany R-M. Batten disease or neuronal ceroid lipofuscinosis. In: *Handbook of clinical neurology, Neurodystrophies and neurolipidoses.* N.Y.: Elsevier; 1996. pp. 671-900.
2. Zhong N. Neuronal ceroid lipofuscinoses and possible pathogenic mechanism. *Mol Genet Metab* 2000; 71(1-2): 195-206.
3. Kida et al. Cellular pathology and pathogenic aspects of neuronal ceroid lipofuscinoses. *Adv Genet.* 2001; 45:35-68.
4. Guo et al. A disrupted homolog of the CLN3 or Juvenile Neuronal Ceroid Lipofuscinosis gene in *Sacchromyces cerevisiae. Cellular and Molecular Neurology* 1999; 19(5):671-680.
5. Persaud-Sawin et al. Motifs within the CLN3 protein: modulation of cell growth rates and apoptosis. *Hum Mol Genet.* 2002; 11(18):2129-42.
6. Mao et al. Membrane topology of CLN3, the protein underlying Batten disease. *FEBS Letters* 2003; 541:40-46.
7. Dhar et al. Flupirtine blocks apoptosis in Batten patient lymphoblasts and in human postmitotic CLN3- and CLN2-deficient neurons. *Annals of Neurology* 2002; 51(4):448-466.
8. Kieseier et al. Leukocytes in neuronal ceroid-lipofuscinoses: function and apoptosis. *Brain Dev* 1997; 19(5):317-22.
9. Lane et al. Apoptosis as the mechanism of neurodegeneration in Batten's disease. *J Neurochem* 1996; 67(2):677-83.
10. Cao et al. Autophagy is disrupted in a knock-in mouse model of juvenile neuronal ceroid lipofuscinosis. *J Biol. Chem.* 2006; 281(29):20483-93.
11. Puranam et al. Upregulation of Bcl-2 and elevation of ceramide in Batten disease. *Neuropediatrics* 1997; 28(1):37-41.
12. Rylova et al. The CLN3 gene is a novel molecular target for cancer drug discovery. *Cancer Res* 2002; 62(3):801-8.
13. Jarvela et al. Defective intracellular transport of CLN3 is the molecular basis of Batten disease (JNCL). *Hum Mol Genet.* 1999; 8(6):1091-8.
14. Pearce & Sherman. A yeast model for the study of Batten disease. *Proc. Natl. Acad. Sci. USA* 1998; 95(12):6915-8.
15. Katz et al. A mouse knock out model for Juvenile Neuronal Ceroid Lipofuscinosis (Batten Disease). *Journal of Neuroscience Research* 1999; 57:551-556.
16. Haskell et al. Batten disease: evaluation of CLN3 mutations on protein localization and function. *Hum Mol Genet.* 2000; 9(5):735-44.

17. Luiro et al. CLN3 protein is targeted to neuronal synapses but excluded from synaptic vesicles: new clues to Batten disease. *Hum Mol Genet.* 2001; 10(19):2123-31.
18. Margraf et al. Tissue expression and subcellular localization of CLN3, the Batten disease protein. *Mol Genet Metab* 1999; 66(4):283-9.
19. Kremmidiotis et al. The Batten disease gene product (CLN3p) is a Golgi integral membrane protein. *Hum Mol Genet.* 1999; 8(3):523-31.
20. Persaud-Sawin et al. A galactosylceramide binding domain is involved in trafficking of CLN3 from Golgi to rafts via recycling endosomes. *Pediatric Res.* 2004; 56(3) 449-63.
21. Mahfoud et al. Identification of a common sphingolipid-binding domain in Alzheimer, prion, and HIV-1 proteins. *J Biol Chem* 2002; 277(13):11292-6.
22. Huang et al. Emodin inhibits tumor cell adhesion through disruption of the membrane lipid Raft-associated integrin signaling pathway. *Cancer Res.* 2006; 66(11):5807-15. 10
23. Patschan et al. Probing lipid rafts with proximity imaging: actions of proatherogenic stimuli. *Am J Physiol Heart Circ Physiol.* 2006; 290(6)H2210-9.
24. Gombos et al. Cholesterol and sphingolipids as lipid organizers of the immune cells' plasma membrane: their impact on the functions of MHC molecules, effector T lymphocytes and T-cell death. *Immunol Lett.* 2006; 104(1-2):59-69.
25. Brugger et al. The HIV lipidome: a raft with an unusual composition. *Proc Natl Acad Sci USA.* 2006; 103(8):2641-6.
26. Simons & Ikonen. Functional rafts in cell membranes. *Nature* 1997; 387:569-573.
27. Miyaji et al. Role of membrane sphingomyelin and ceramide in platform formation for Fas-mediated apoptosis. *J Exp Med.* 2005; 202(2):249-59.
28. Nayak & Hui. The role of lipid microdomains in virus biology. *Subcell Biochem.* 2004; 37:443-91.
29. Zaas et al. The role of lipid rafts in the pathogenesis of bacterial infections. *Biochim Biophys Acta* 2005; 1746(3): 305-313.
30. Jolly & Sattentau. Human immunodeficiency virus type 1 virological synapse formation in T cells requires lipid raft integrity. *J. Virol.* 2005; 79(18):12088-94.
31. Hering et al. Lipid rafts in the maintenance of synapses, dendritic spines, and surface AMPA receptor stability. *J. Neurosci.* 2003; 23(8):3262-71.
32. London & Brown. Insolubility of lipids in triton X-100: physical origin and relationship to sphingolipid/cholesterol membrane domains (rafts). *Biochim Biophys Acta.* 2000; 1508(1-2):182-95.
33. Kilkus et al. Ceramide in rafts (detergent-insoluble fraction) mediates cell death in neurotumor cell lines. *J Neurosci Res.* 2003; 72(1):65-75.
34. Atshaves et al. Sterol carrier protein-2 selectively alters lipid composition and cholesterol dynamics of caveolae/lipid raft vs. nonraft domains in L-cell fibroblast plasma membranes. Biochemistry. 2003; 42(49):14583-98.
35. Pullarkat & Morris. Farnesylation of Batten disease CLN3 protein. *Neuropediatrics* 1997; 28(1):42-4.
36. Eramo et al. CD95 death inducing signaling complex formation and internalization occur in lipid rafts of type I and type II cells. *Eur J. Immunol.* 2004; 34(7):1930-40.
37. Sakurai et al. Fragmentation of the Golgi apparatus of the ballooned neurons in patients with corticobasal degeneration and Creutzfeldt-Jakob disease. *Acta Neuropathology* 2000; 100:270-274.
38. Fujita et al. Fragmentation of the Golgi apparatus of the anterior horn cells in patients with familial amyotrophic lateral sclerosis with SOD1 mutations and posterior column involvement. *J Neurol Sci.* 2000; 174(2):137-40.
39. Liazoghli et al. Fragmentation of the Golgi apparatus induced by the overexpression of wild-type and mutant human tau forms in neurons. *Am J. Pathol.* 2005; 166(5): 1499-1514.
40. Jeckel et al. Glucosylceramide is synthesized at the cytosolic surface of various Golgi subfractions. *J. Cell Biol.* 1992; 117(2):259-67.
41. Sprong et al. Association of the Golgi UDP-Galactose Transporter with UDP-Galactose:Ceramide Galactosyltransferase Allows UDPGalactose Import in the Endoplasmic Reticulum. *Mol Biol Cell.* 2003; 14(8):3482-3493.
42. Davidson & Chen. Structural biology. Flipping lipids: is the third time the charm? *Science.* 2005; 308(5724):963-5.
43. Eckford & Sharom. The reconstituted P-glycoprotein multidrug transporter is a flippase for glucosylceramide and other simple glycosphingolipids. *Biochem J.* 2005; 389(2):517-26.
44. Gammon et al. Isolation of two glycolipid transfer proteins from bovine brain: reactivity toward gangliosides and neutral glycosphingolipids. *Biochemistry.* 1987; 26(19): 6239-43.
45. Nylund & Mattjus. Protein mediated glycolipid transfer is inhibited FROM sphingomyelin membranes but enhanced TO sphingomyelin containing raft like membranes. *Biochim Biophys Acta.* 2005; 1669(2):87-94.
46. Rao et al. Glycolipid transfer protein interaction with bilayer vesicles: modulation by changing lipid composition. *Biophys J.* 2005; 89(6):4017-28.
47. Hanada et al. Molecular Machinery for Non-vesicular Trafficking of Ceramide. *Nature* 2003; 426(6968):803-809.
48. Borst et al. ABC transporters in lipid transport. *Biochim Biophys Acta.* 2000; 1486(1):128-44.
49. Dean & Chimini. The human ATP-binding cassette (ABC) transporter superfamily. *J. Lipid Res.* 2001; 42:1007-1017.
50. Gottesman & Ambudkar. Overview: ABC transporters and human disease. *J. Bioenerg. Biomembr.* 1992; 33:453-458.
51. Higgins & Gottesman. Is the multidrug transporter a flippase? *Trends Biochem. Sci.* 1992; 17:18-21.
52. Levine T P. Membrane contact sites, a network for short-range intracellular communication. *Trends in Cell Biology* 2004; 9:483-490.
53. Nutikka & Lingwood. Generation of receptor-active, globotriaosyl ceramide/cholesterol lipid 'rafts' in vitro: A new assay to define factors affecting glycosphingolipid receptor activity. *Glycoconjugate Journal* 2004; 20(1):33-38.
54. Koumanov et al. Comparative lipid analysis and structure of detergent-resistant membrane raft fractions isolated from human and ruminant erythrocytes. *Arch Biochem Biophys.* 2005; 434(1):150-8.
55. Saravanan et al. Specific downregulation and mistargeting of the lipid raft-associated protein MAL in a glycolipid storage disorder. *Neurobiology of Disease* 2004; 162:396-406.
56. O'Brie &, Sampson. Lipid composition of the normal human brain: gray matter, white matter, and myelin. *Journal of Lipid Research* 1965; 6.
57. Vos et al. Metabolic and functional aspects of sulfogalactolipids. *Biochim Biophys Acta.* 1994; 1211(2):125-49.
58. Boggs & Wang. Co-clustering of galactosylceramide and membrane proteins in oligodendrocyte membranes on interaction with polyvalent carbohydrate and prevention by an intact cytoskeleton. *Journal of Neuroscience Research* 2004; 76(3):342-355.
59. Hirahara et al. Sulfatide is a negative regulator of oligodendrocyte differentiation: development in sulfatide-null mice. *Glia* 2004; 45(3):269-77.

60. Dyer & Benjamins. Galactocerebroside and sulfatide independently mediate $Ca^{2+}$ responses in oligodendrocytes. *J Neurosci Res.* 1991; 30(4):699-711.
61. Puranam et al. CLN3 defines a novel antiapoptotic pathway operative in neurodegeneration and mediated by ceramide. *Mol Genet Metab* 1999; 66(4):294-308.
62. Persaud-Sawin et al. Neuronal Ceroid Lipofuscinosis: A Common Pathway? *Pediatric Research* 2007; 61(2):146-152.
63. Stagg et al. From cancer immunosurveillance to cancer immunotherapy. *Immunological Reviews* 220(1):82-101 (2007)
64. Nicol et al. Human invariant V[alpha]24+ natural killer T cells activated by [alpha]-galactosylceramide (KRN7000) have cytotoxic anti-tumour activity through mechanisms distinct from T cells and natural killer cells. *Immunology* 99(2):229-234 (2000)
65. Sullivan & Kronenberg. Activation or anergy: NKT cells are stunned by [alpha]-galactosylceramide. *Journal of Clinical Investigation* 115(9):2328-2329 (2005)
66. Matsuyoshi et al. Therapeutic effect of [alpha]-galactosylceramide-loaded dendritic cells genetically engineered to express SLC/CCL21 along with tumor antigen against peritoneally disseminated tumor cells *Cancer Science* 96(12):889-896 (2005)
67. Zaini et al. OX40 ligand expressed by DCs costimulates NKT and CD4+ Th cell antitumor immunity in mice *Journal of Clinical Investigation* 117(11):3330-3338 (2007)
68. Nagaraj et al. Dendritic cells pulsed with alpha-galactosylceramide induce anti-tumor immunity against pancreatic cancer in vivo *International Immunology* 18(8):1279-1283 (2006)

TABLE 1

Levels of galactosylceramide (GalCer) in lipid rafts, Golgi and ER fractions mouse brain. GalCer is diminished in lipid rafts and retained in the Golgi in homozygous Δex7/8 knock-in mouse brain.

| Fractions | | μg GalCer/μg Phos |
|---|---|---|
| Lipid rafts | Wild type | 44.28 |
| | CLN3 -/- | 29.85 |
| Golgi | Wild type | 139.39 |
| | CLN3 -/- | 691.89 |
| ER | Wild type | 427.14 |
| | CLN 3 -/- | 482.53 |

What is claimed is:

1. A method for treating a disorder associated with or caused by a deficiency in a gene product of a CLN3 gene, defective in juvenile neuronal ceroid lipofuscinosis (JNCL), in a subject, comprising administering to the subject galactosylceramide in an amount effective to treat the disorder, thereby treating the disorder in the subject, wherein the galactosylceramide is administered in the absence of an exogenous nucleic acid.

2. A method of treating a disorder associated with or caused by a deficiency in a gene product of a CLN3 gene, defective in juvenile neuronal ceroid lipofuscinosis (JNCL), in a subject, comprising administering to the subject a heterologous nucleic acid comprising a heterologous nucleotide sequence encoding an enzyme in the synthetic pathway of a sphingolipid of galactosylceramide, wherein the enzyme is selected from the group consisting of sphingomyelin synthase, galactosylceramide transferase, glucosylceramide synthase, lactosylceramide synthase, GB3/CD77 synthase and any combination thereof, in an amount effective to treat the disorder, thereby treating the disorder in the subject.

3. A method of reducing apoptosis of cells in a subject, wherein the apoptosis is due to or results from a deficiency in a gene product of a CLN3 gene, defective in juvenile neuronal ceroid lipofuscinosis (JNCL), comprising administering to the subject galactosylceramide an in an amount effective to reduce apoptosis, thereby reducing apoptosis of cells in the subject, wherein the galactosylceramide is administered in the absence of an exogenous nucleic acid.

4. A method of correcting aberrant ultrastructural morphology of a cell in a subject, wherein the aberrant ultrastructural morphology of the cell is due to or results from a deficiency in a gene product of a CLN3 gene, defective in juvenile neuronal ceroid lipofuscinosis (JNCL), comprising administering to the subject galactosylceramide in an amount effective to correct aberrant ultrastructural morphology, thereby correcting aberrant ultrastructural morphology of the cell in the subject, wherein the galactosylceramide is administered in the absence of an exogenous nucleic acid.

5. A method of correcting aberrant lipid stoichiometry of lipid rafts in a cell of a subject, wherein the aberrant lipid stoichiometry of lipid rafts in the cell is due to or results from a deficiency in a gene product of a CLN3 gene, defective in juvenile neuronal ceroid lipofuscinosis (JNCL), comprising administering to the subject galactosylceramide in an amount effective to correct aberrant lipid stoichiometry of lipid rafts, thereby correcting aberrant lipid stoichiometry of lipid rafts

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial
<220> FEATURE:
<223> OTHER INFORMATION: HS1 siRNA sequence for CLN3 knockdown

<400> SEQUENCE: 1
tcacgatttg actgcaactc tg                                              22
``` in the cell of the subject, wherein the galactosylceramide is administered in the absence of an exogenous nucleic acid.

6. The method of claim 1, wherein the subject is a human.

7. The method of claim 2, wherein the subject is a human.

8. The method of claim 1, wherein the amount of the galactosylceramide administered to the subject is in the range of about 0.1 ug/kg to about 100 ug/kg.

9. The method of claim 1, wherein the galactosylceramide is administered subcutaneously, intravenously, intrathecally and/or intraperitoneally.

10. The method of claim 2, wherein the heterologous nucleic acid is in a vector.

11. A method of reducing apoptosis of cells in a subject, wherein the apoptosis is due to or results from a deficiency in a gene product of a CLN3 gene, defective in juvenile neuronal ceroid lipofuscinosis (JNCL), comprising administering to the subject a heterologous nucleic acid comprising a heterologous nucleotide sequence encoding an enzyme in the synthetic pathway of galactosylceramide, wherein the enzyme is selected from the group consisting of sphingomyelin synthase, galactosylceramide transferase, glucosylceramide synthase, lactosylceramide synthase, GB3/CD77 synthase and any combination thereof, in an amount effective to reduce apoptosis, thereby reducing apoptosis of cells in the subject.

12. The method of claim 11, wherein the heterologous nucleic acid is in a vector.

13. A method of correcting aberrant ultrastructural morphology of a cell in a subject, wherein the aberrant ultrastructural morphology of the cell is due to or results from a deficiency in a gene product of a CLN3 gene, defective in juvenile neuronal ceroid lipofuscinosis (JNCL), comprising administering to the subject an effective amount of a heterologous nucleic acid comprising a heterologous nucleotide sequence encoding an enzyme in the synthetic pathway of galactosylceramide, wherein the enzyme is selected from the group consisting of sphingomyelin synthase, galactosylceramide transferase, glucosylceramide synthase, lactosylceramide synthase, GB3/CD77 synthase and any combination thereof, in an amount effective to correct aberrant ultrastructural morphology, thereby correcting aberrant ultrastructural morphology of the cell in the subject.

14. The method of claim 13, wherein the heterologous nucleic acid is in a vector.

15. A method of correcting aberrant lipid stoichiometry of lipid rafts in a cell of a subject, wherein the aberrant lipid stoichiometry of lipid rafts in the cell is due to or results from a deficiency in a gene product of a CLN3 gene, defective in juvenile neuronal ceroid lipofuscinosis (JNCL), comprising administering to the subject an effective amount of a heterologous nucleic acid comprising a heterologous nucleotide sequence encoding an enzyme in the synthetic pathway of galactosylceramide, wherein the enzyme is selected from the group consisting of sphingomyelin synthase, galactosylceramide transferase, glucosylceramide synthase, lactosylceramide synthase, GB3/CD77 synthase and any combination thereof, in an amount effective to correct aberrant lipid stoichiometry of lipid rafts, thereby correcting aberrant lipid stoichiometry of lipid rafts in the cell of the subject.

16. The method of claim 15, wherein the heterologous nucleic acid is in a vector.

17. The method of claim 1, wherein the galactosylceramide is administered to the subject over the remaining life time of the subject.

* * * * *

UNITED STATES PATENT AND TRADEMARK OFFICE
CERTIFICATE OF CORRECTION

PATENT NO.        : 8,242,086 B2
APPLICATION NO.   : 12/617318
DATED             : August 14, 2012
INVENTOR(S)       : Boustany Page 1 of 1

It is certified that error appears in the above-identified patent and that said Letters Patent is hereby corrected as shown below:

In the Specification:
Column 14, Line 54:
    Please correct "literature (see, e.g.," to read -- literature. --

Column 19, Line 17: Please correct "(fractions ⅔)" to read -- (fractions 2/3) --

Column 22, Line 60: Please correct "6 μmol" to read -- 6 pmol --

Column 26, Line 3: Please correct "CLN3 Aex718" to read -- CLN3 Δex7/8 --

Column 30, Line 52, Reference 11:
    Please correct "BcI-2" to read -- Bcl-2 --

In the Claims:
Column 34, Claim 2, Lines 15 and 16:
    Please correct "synthetic pathway of a sphingolipid of galactosylceramide,"
    to read -- synthetic pathway of galactosylceramide, --

Claim 3, Line 26: Please correct "galactosylceramide an in an amount"
        to read -- galactosylceramide in an amount --

Signed and Sealed this
Ninth Day of April, 2013

Teresa Stanek Rea
*Acting Director of the United States Patent and Trademark Office*